(12) United States Patent
Red-Horse et al.

(10) Patent No.: US 10,543,235 B2
(45) Date of Patent: Jan. 28, 2020

(54) PERICYTES ARE INTERMEDIATE PROGENITORS FOR EPICARDIAL DERIVED CORONARY ARTERY SMOOTH MUSCLE

(71) Applicant: The Board of Trustees of the Leland Stanford Junior University, Stanford, CA (US)

(72) Inventors: Kristy Red-Horse, San Carlos, CA (US); Katharina Volz, San Francisco, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 126 days.

(21) Appl. No.: 15/582,289

(22) Filed: Apr. 28, 2017

(65) Prior Publication Data

US 2017/0312319 A1    Nov. 2, 2017

Related U.S. Application Data

(60) Provisional application No. 62/329,767, filed on Apr. 29, 2016.

(51) Int. Cl.
*A61K 35/44* (2015.01)
*C12N 5/071* (2010.01)

(52) U.S. Cl.
CPC ............ *A61K 35/44* (2013.01); *C12N 5/0691* (2013.01)

(58) Field of Classification Search
None
See application file for complete search history.

(56) References Cited

U.S. PATENT DOCUMENTS

| | | | | |
|---|---|---|---|---|
| 5,266,480 | A * | 11/1993 | Naughton | A61B 90/00 435/371 |
| 2007/0264239 | A1* | 11/2007 | Huard | C12N 5/0657 424/93.7 |
| 2008/0108090 | A1* | 5/2008 | Evans | A01K 67/0275 435/7.21 |
| 2008/0213235 | A1* | 9/2008 | Katz | A61K 48/00 424/93.21 |
| 2009/0021170 | A1* | 1/2009 | Okada | H01J 11/12 313/586 |
| 2009/0148421 | A1* | 6/2009 | Anversa | C12N 5/0692 424/93.7 |
| 2009/0175833 | A1* | 7/2009 | Dore-Duffy | C12N 5/0692 424/93.7 |

OTHER PUBLICATIONS

Avolio et al. Combined intramyocardial delivery of human pericytes and cardiac stem cells additively improves the healing of mouse infarcted hearts through stimulation of vascular and muscular repair. Circ Res. 2015;116:e81-e94 (Year: 2015).*
Armulik et al., "Pericytes: Developmental, Physiological, and Pathological Perspectives, Problems, and Promises", Developmental Cell, Aug. 16 2011,pp. 193-215, vol. 21, Issue 2, Elsevier Inc., Amsterdam, Netherlands.
Cappellari et al., Pericytes in Development and Pathology of Skeletal Muscle., Circulation Research, Jul. 19, 2013, pp. 341-347, vol. 113, Issue 3, American Heart Association, Inc., Dallas, TX.
Majesky et al., "Vascular Smooth Muscle Progenitor Cells Building and Repairing Blood Vessels", Circulation Research, Feb. 4, 2011, pp. 365-377, vol. 108, Issue 3, American Heart Association, Inc., Dallas, TX.
McCormick et al., "DNA microarray reveals changes in gene expression of shear stressed human umbilical vein endothelial cells", PNAS, Jul. 31, 2001, pp. 8955-8960, vol. 98 No. 16, PNAS, Washington, DC.
Rinkevich et al., "Identification and prospective isolation of a mesothelial precursor lineage giving rise to smooth muscle cells and fibroblasts for mammalian internal organs, and their vasculature", Nature Cell Biology, Dec. 2012, pp. 1251-1260, 14 (12), Macmillan Publishers Limited, London, United Kingdom.
Theodoris et al.,"Human disease modeling reveals integrated transcriptional and epigenetic mechanisms of NOTCH1 haploinsufficiency", Cell, Mar. 12, 2015, pp. 1072-1086, vol. 160, Issue 6, Elsevier Inc., Amsterdam, Netherlands.
Zhou et al., "TXNIP (VDUP-1, TBP-2): a major redox regulator commonly suppressed in cancer by epigenetic mechanisms", The International Journal of Biochemistry & Cell Biology, Dec. 2011, pp. 1668-1673, vol. 43, Issue 12, Elsevier Inc., Amsterdam, Netherlands.

* cited by examiner

*Primary Examiner* — Blaine Lankford
(74) *Attorney, Agent, or Firm* — Pamela J. Sherwood; Bozicevic, Field & Francis LLP

(57) ABSTRACT

Methods and compositions are provided for regenerating smooth muscle tissue by the provision of a purified population of epicardial-derived pericytes, where the smooth muscle tissue may comprise, without limitation, coronary artery tissue; kidney tissue, etc. Compositions and kits for practicing the methods and/or for use with the systems of the disclosure are also provided.

10 Claims, 19 Drawing Sheets
(19 of 19 Drawing Sheet(s) Filed in Color)

VE-cadherin (Coronary endothelial cells)     SM-MHC (coronary artery smooth muscle)
e13     e14.5     e15.5     e16.5
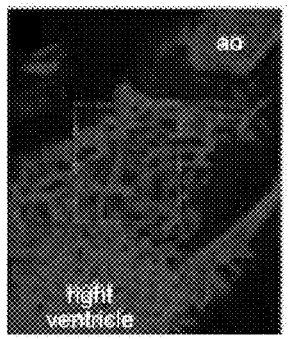 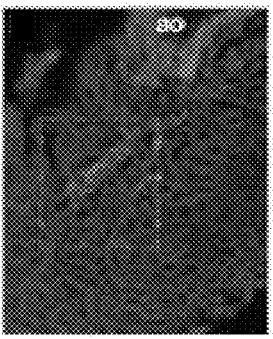 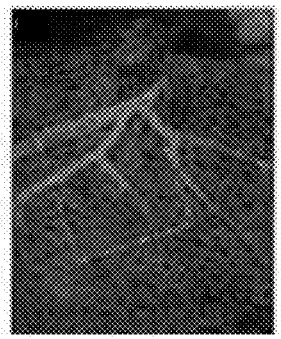 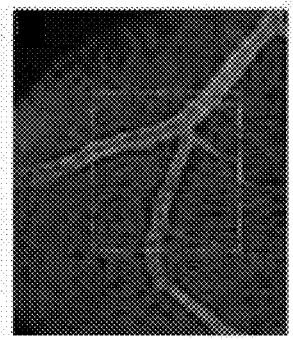
FIG. 1A     FIG. 1B     FIG. 1C     FIG. 1D
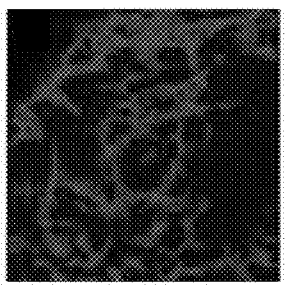 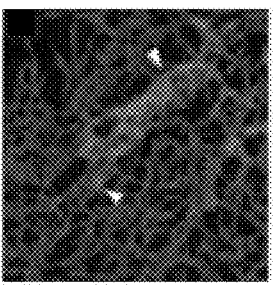 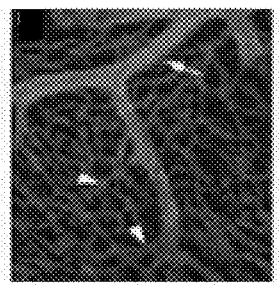 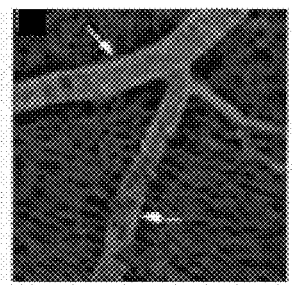
FIG. 1A(1)     FIG. 1B(1)     FIG. 1C(1)     FIG. 1D(1)
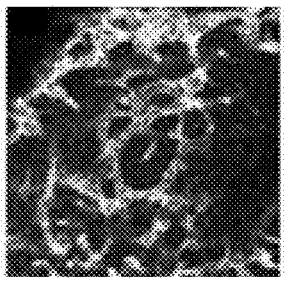 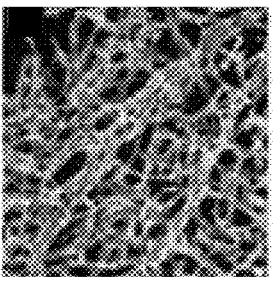 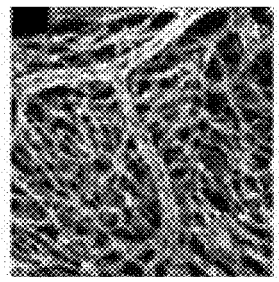 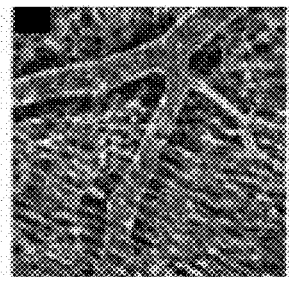
FIG. 1A(2)     FIG. 1B(2)     FIG. 1C(2)     FIG. 1D(2)
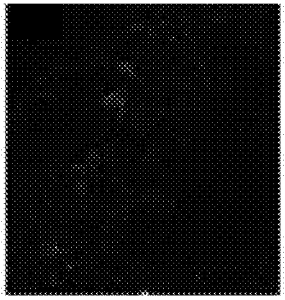  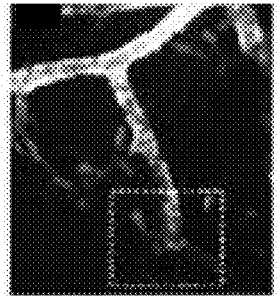 
FIG. 1A(3)     FIG. 1B(3)     FIG. 1C(3)     FIG. 1D(3)

SM-MHC levels in individual mural cells at different regions of the vasculature

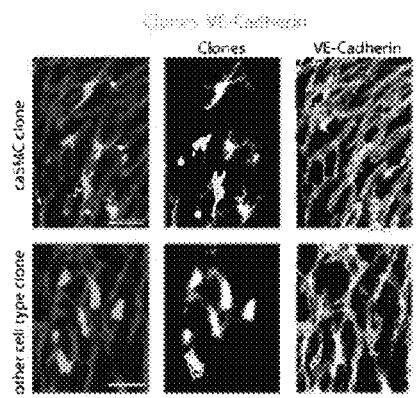
FIG. 2A
FIG. 2B
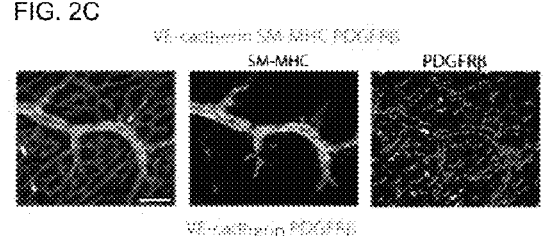
FIG. 2C
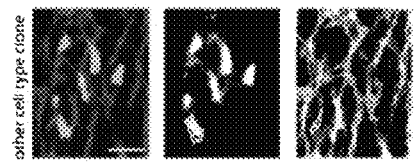
FIG. 2D  FIG. 2E
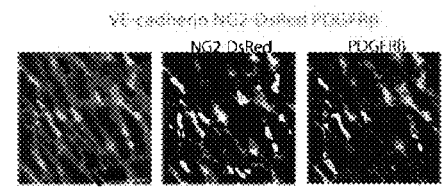
FIG. 2F
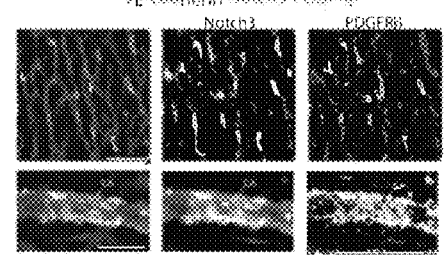
FIG. 2G
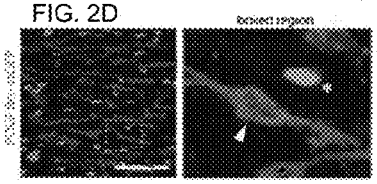
FIG. 2J
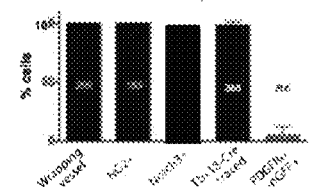
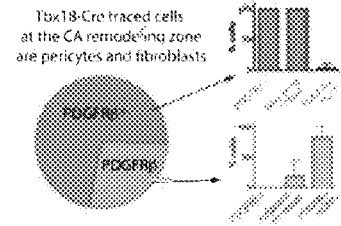
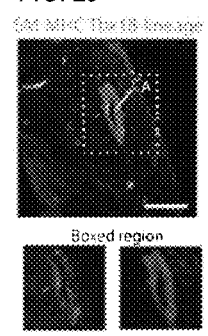
FIG. 2H
FIG. 2I

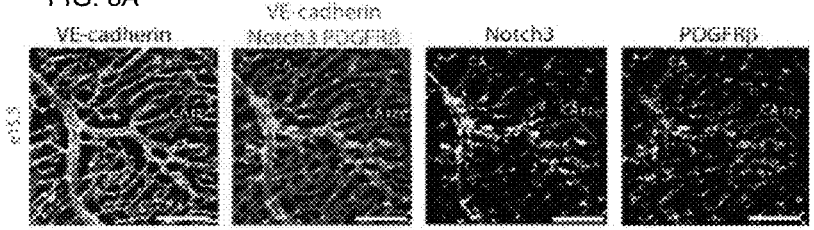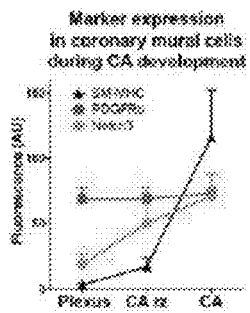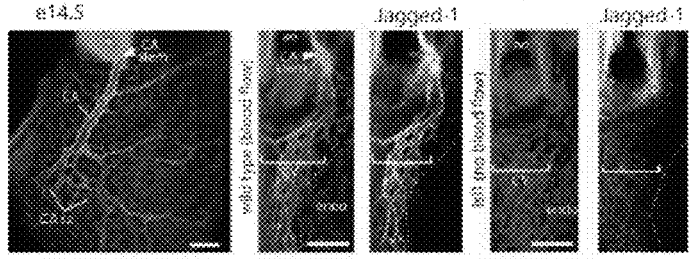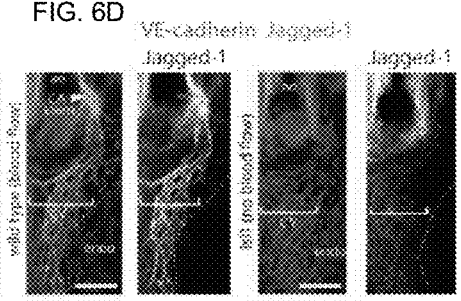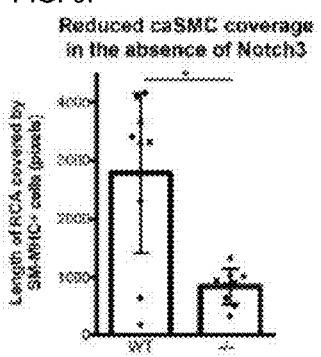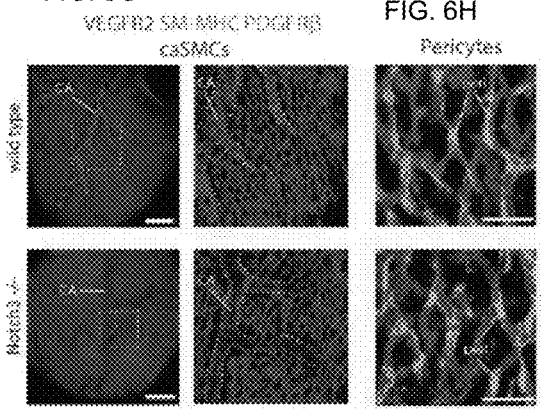

FIG. 9A
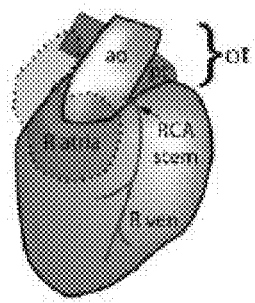
FIG. 9B
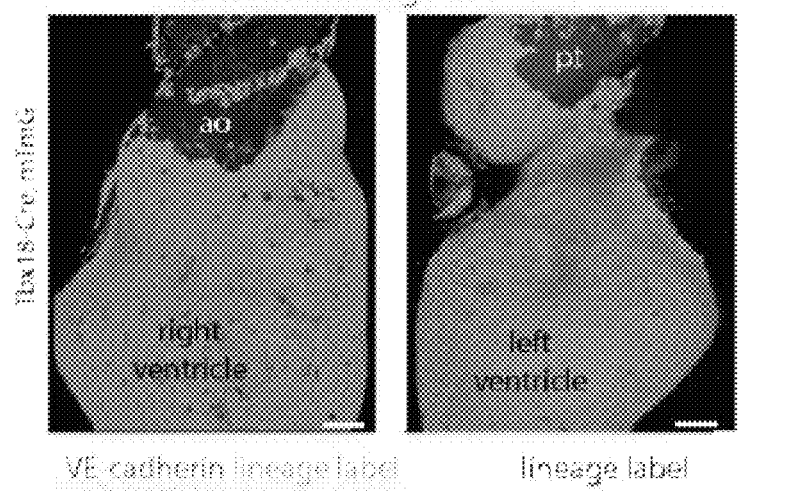
FIG. 9C

FIG. 10A
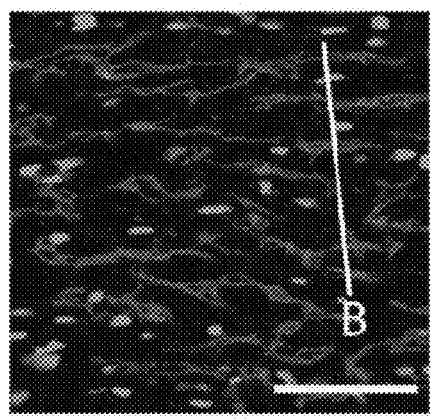
FIG. 10B
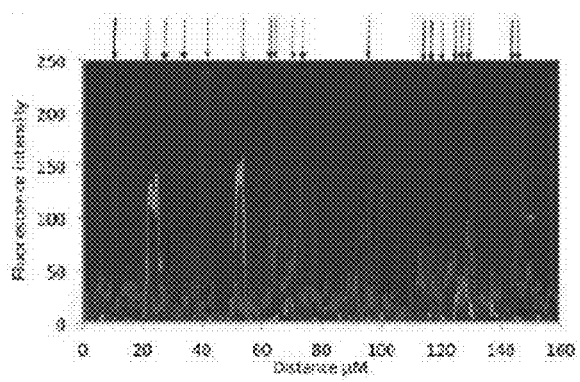
FIG. 10C
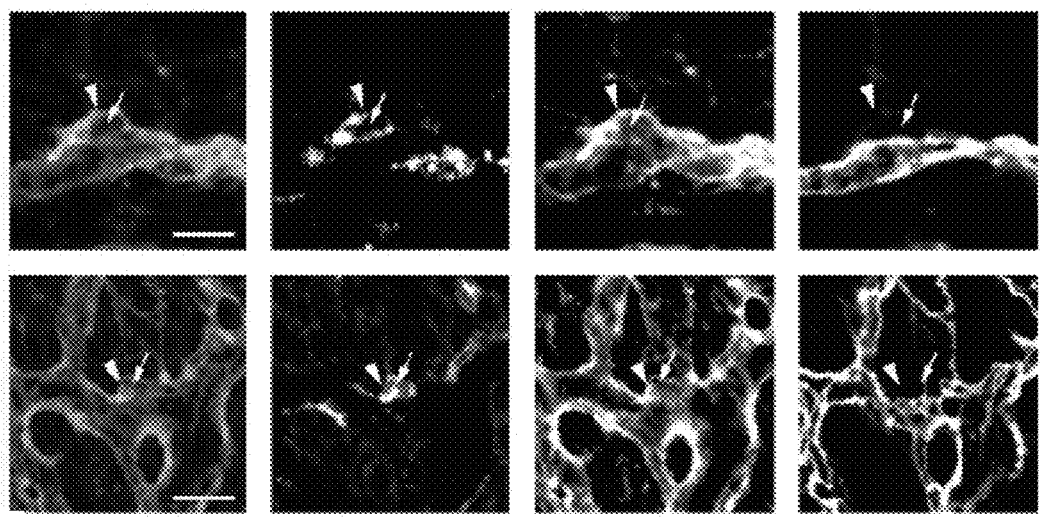
FIG. 10D

Tbx18-lineage (Epi-derived) VE-cadherin
FIG. 12A PDGFRβ
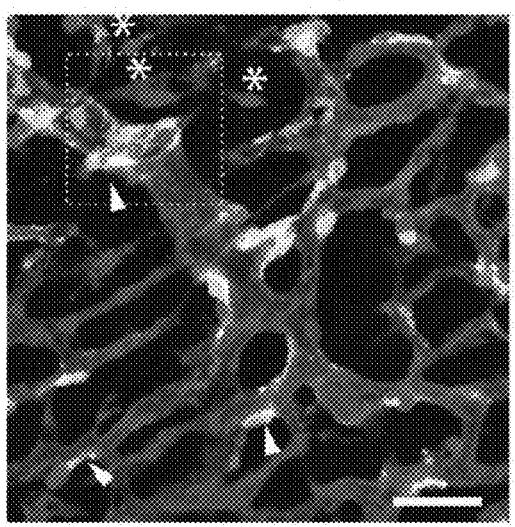
Boxed regions
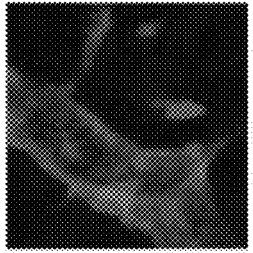 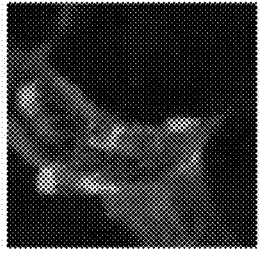
FIG. 12B PDGFRα-nGFP
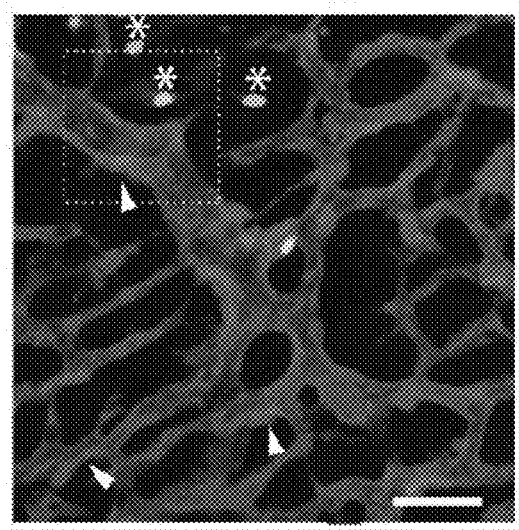
Boxed regions
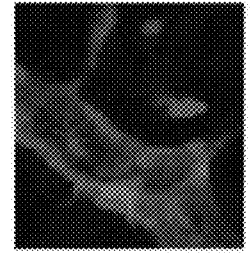 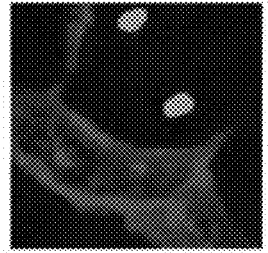

FIG. 13A
Position of cells among Tbx18-derived clones

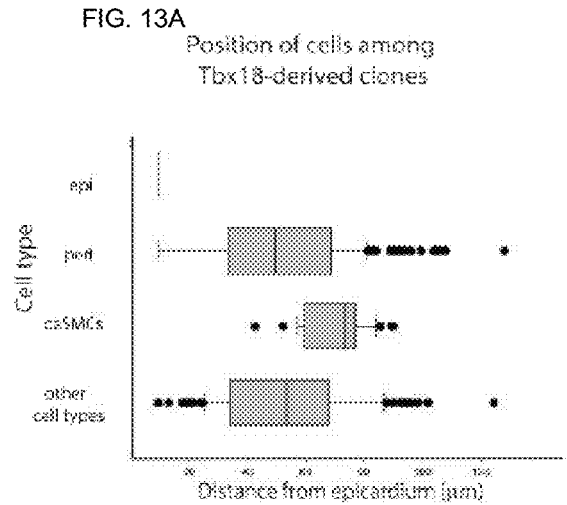

FIG. 13C
Distribution of cells within Tbx18-Cre-induced clones

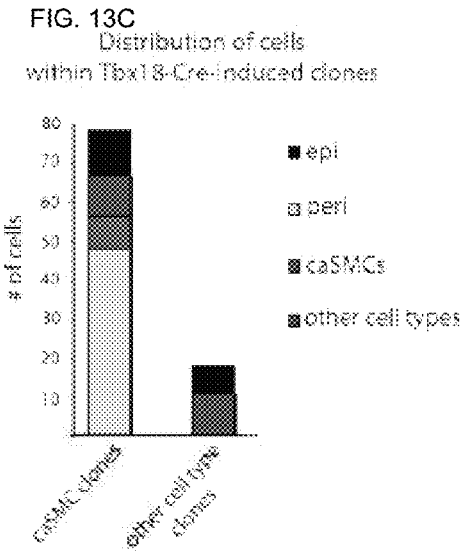

FIG. 13B
e15.5 clone composition: 30 Epicardial, 79 Pericytes, 5 caSMCs
Tbx18 Cre - induced Clones VE-cadherin (endothelial cells) SM-MHC (caSMCs)

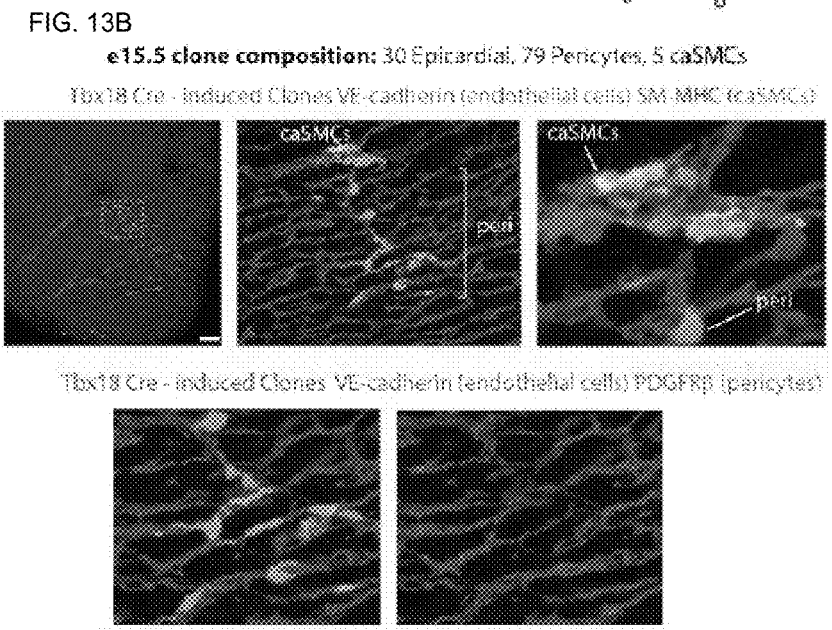

Tbx18 Cre - induced Clones VE-cadherin (endothelial cells) PDGFRβ (pericytes)

FIG. 13D   Adult clone composition: 101 Pericytes, 5 caSMCs
Tbx18 Cre - induced Clones VEGFR2 SM-MHC (caSMCs)                    Boxed region:

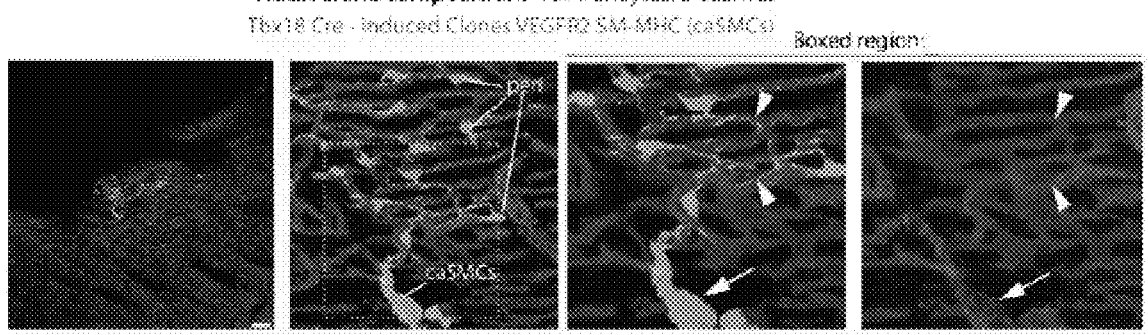

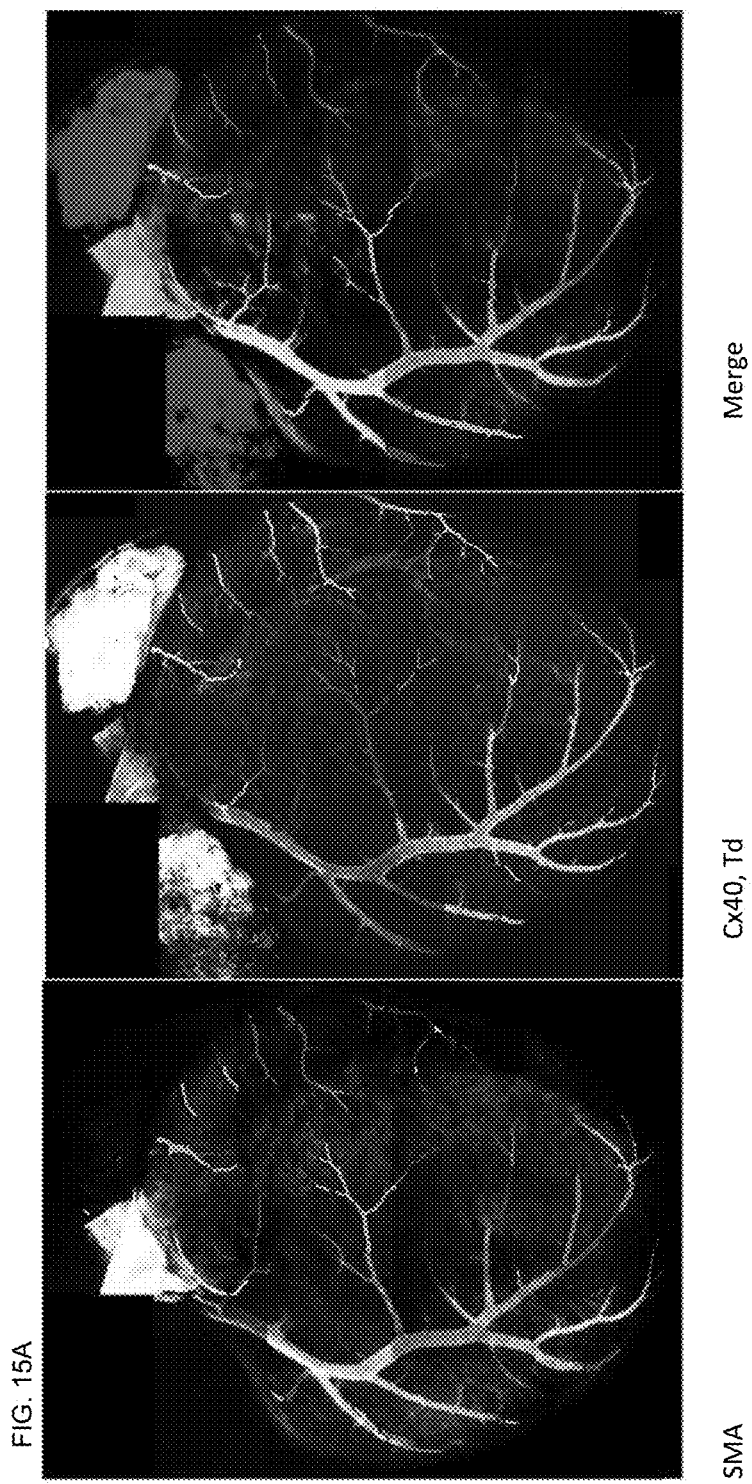

PERICYTES ARE INTERMEDIATE PROGENITORS FOR EPICARDIAL DERIVED CORONARY ARTERY SMOOTH MUSCLE

CROSS REFERENCE

This application claims benefit of U.S. Provisional Patent Application No. 62/329,767, filed Apr. 29, 2016, which applications are incorporated herein by reference in their entirety.

BACKGROUND

Arteries are the large blood vessels that carry oxygenated blood away from the heart to all the tissues and organs in the body. They are integral to the proper function of each organ since their disruption severely compromises the ability of each tissue to perform. As with all blood vessels, arteries contain a single endothelial cell layer facing the blood lumen (tunica intima), but, in addition, they have several concentric layers of smooth muscle, which makes up the majority of the artery (tunica media) and provides it with structural integrity and contractility. In most arteries the endothelial cell layer is separated from the smooth muscle cell layer by an internal elastic membrane. Furthermore, elastic fibers and other structural components are embedded within the smooth muscle cell layers. This allows arteries to remain compliant in response to the pulsatile blood flow found directly downstream of the heart. The outer layer of the arterial wall entails an adventitial layer of fibroblasts embedded in a collagen matrix (tunica externa). Despite the relatively constant structure of arteries serving each organ, their construction during development can vary from site to site in terms of cellular origins and morphogenesis. Because of this heterogeneity, there is still much to learn about the development and biological regulation of organ-specific arteries.

Angiogenesis and vasculogenesis are processes involved in the growth of blood vessels. Angiogenesis is the process by which new blood vessels are formed from extant capillaries, while vasculogenesis involves the growth of vessels deriving from endothelial progenitor cells. Angiogenesis and vasculogenesis, and the factors that regulate these processes, are important in embryonic development, inflammation, and wound healing, and also contribute to pathologic conditions such as tumor growth, diabetic retinopathy, rheumatoid arthritis, and chronic inflammatory diseases.

Microvascular perivascular cells ("pericytes") are defined by their location in vivo. The pericyte is a small ovoid shaped cell with many finger-like projections that parallel the capillary axis and partially surround an endothelial cell in a microvessel. Pericytes share a common basement membrane with the endothelial cell. Pericytes are elongated cells with the power of contraction that have been observed to have a variety of functional characteristics. Some of the pericyte functional characteristics observed in vivo and in vitro are that they regulate endothelial cell proliferation and differentiation, contract in a manner that either exacerbates or reduces endothelial cell junction inflammatory leakage, synthesize and secrete a wide variety of vasoactive auto-regulating agonists, and synthesize and release structural constituents of the basement membrane and extracellular matrix.

Pericytes play an important role in angiogenesis and vessel maturation. During angiogenesis pericytes prevent vessel regression and promote endothelial quiescence. Generally, high pericyte coverage is observed in peripheral tissues, supporting a role of pericytes in regulating orthostatic blood pressure. High pericyte coverage also correlates with barrier function for instance in the blood-brain barrier and a low endothelial turnover rate. Therefore, besides a general role in vessel formation, pericytes seem to have tissue-specific function including endothelial barrier function and blood pressure regulation of microvessels. While the role of pericytes has been extensively studied during angiogenesis, less is known about their involvement in arteriogenesis.

The vasculature is a network of endothelial-lined tubes covered with mural cells where pericytes associate with small vessels and smooth muscle surrounds larger arteries and veins. Because these cells exist in close proximity, vascular biologists have long wondered whether pericytes and smooth muscle cells interconvert. However, direct evidence has been restricted by limited experimental tools and a lack of knowledge about when and where such differentiation events might occur. Knowing whether pericytes and smooth muscle differentiate into each other, and the mechanisms that stimulate this process, has the potential to impact clinical treatments for cardiovascular disease. Our research has discovered that in the heart during embryonic development, pericytes are the progenitors of coronary artery smooth muscle, and that Notch signaling stimulates the pericyte to smooth muscle transition. Understanding coronary artery biology could identify clinical treatments for coronary artery disease.

Coronary artery smooth muscle development remains a poorly understood process. Current methods of coronary artery regeneration fail to produce meaningful repair following cardiovascular injury, because of a lack of knowledge on progenitor cell populations and the signaling pathways that activate their differentiation. The discovery that pericytes are epicardial-derived coronary artery smooth muscle progenitors could have implications for regenerative medicine, as this knowledge could reveal new progenitor cells and targetable pathways for coronary disease.

SUMMARY

Methods and compositions are provided for providing or regenerating smooth muscle tissue to a vessel in need thereof by contacting a vessel with an effective dose of epicardial-derived pericytes. In some embodiments, the vessel is an artery. In some embodiments the vessel is a coronary artery. Aspects of the method also include administering to the individual a dose of an isolated population of epicardial-derived pericytes effective to generate or regenerate smooth muscle tissue, e.g. a coronary artery; or developing kidney.

In some embodiments methods and compositions are provided for treatment of devascularized tissue by stimulating angiogenesis in a tissue in need thereof. Aspects of the method include contacting a devascularized tissue with an effective dose of epicardial-derived pericytes. Aspects of the method also include administering to the individual a dose of an isolated population of epicardial-derived pericytes effective to stimulate angiogenesis.

In some embodiments of the invention, methods are provided for purification of pericytes from epicardial tissue. In related embodiments, purified populations of pericytes thus isolated are provided, e.g. where at least about 50% of cells in the population, at least about 60%, at least about 70%, at least about 80%, at least about 90%, at least about 95% are of the desired phenotype. The pericytes of the invention can be obtained from epicardial tissue, which may be fetal, neonatal, or adult tissue, and can be isolated by selecting for cells that positively express NG2, Notch3 and PDGFRβ. The cells may be negatively selected for expression of jagged, i.e. the pericytes of the invention are jagged negative.

In some embodiments of the invention, methods are provided for activation of resident epicardial-derived pericytes to differentiate into smooth muscle cells. Aspects of the method include inducing differentiation of resident pericytes via drug-mediated activation of cell signaling pathways. In some embodiments, a pathway is activated by contacting a Notch agonist. In some embodiments, a fluid sheer stress pathway is activated by an agonist of VEGFR2 or VEGFR3. In some embodiments, differentiation of resident pericytes is accomplished by inducing expression of transcription factor Kruppel-like factor 2 (KLF2). In some embodiments, differentiation is accomplished by inducing expression of endothelial NOS (eNOS). In some embodiments, differentiation is accomplished by inducing expression of phosphoinositide 3-kinase (PI3K). In certain such embodiments the activating agent, e.g. a Notch agonist, a VEGFR2 agonist, or a VEGFR3 agonist, is localized in epicardial tissue, e.g. by localized drug depot or implant.

Compositions and kits for practicing the methods and/or for use with the systems of the disclosure are also provided.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1I. Coronary artery smooth muscle differentiation is initiated early during vascular remodeling. (FIG. 1A-D(3)) Whole mount confocal images of the developing right coronary artery at embryonic (e) days 13 (FIG. 1A-A(3)), 14.5 (FIG. 1B-B(3)), 15.5 (FIG. 1C-C(3)), and 16.5 (FIG. 1D-D(3)) immunostained with VE-cadherin (blue) and SM-MHC (red). Higher magnification views (z-stack subsets) from boxed regions (FIG. 1A(1)-D(1)) and separated channels (FIG. 1A(2)-D(3)) show that smooth muscle first appears at early remodeling zones (arrowheads) and further accumulates as these transform into coronary arteries (arrows). (FIG. 1E) Schematic representation showing coronary artery (CA) smooth muscle cell (red) development coincident with aortic attachment and initiation of blood flow at the coronary artery remodeling zone (CA rz). (FIG. 1F) Boxed region in FIG. 1C(3) highlighting SM-MHC$^{low}$ cells (arrowheads) at the remodeling zone in comparison to the higher expression in cells surrounding a more mature coronary artery (arrow). (FIG. 1G) Histogram plotting SM-MHC expression shows that mural cells of the remodeling zone are SM-MHC$^{low}$ while those around mature arteries are SM-MHC$^{high}$ (n=16 cells/region from 4 embryos). (FIG. 1H) Histogram plotting distance of SM-MHC$^{low}$ cells from the epicardium (n=22 cells from 5 hearts). (FIG. 1I) Proposed model where an intermediate progenitor (IP) bridges epicardial cells (Epi) and coronary artery smooth muscle. Ao, aorta; pt, pulmonary trunk. Scale bars, 100 µm.

FIG. 2A-2J. Characterization of epicardial-derived pericytes in the developing heart (A-G) Whole mount confocal images of hearts immunostained with the indicated antibodies and/or fluorescent labels. (FIG. 2A) Coronary artery smooth muscle cell (caSMC) containing clones (blue) always include pericyte-like sister cells with long extended processes (arrows) that travel along VE-cadherin$^+$ blood vessels (red). (FIG. 2B) Cells within clones not containing caSMCs (other cell type clone) are generally located in between vessels. (FIG. 2C) Smooth muscle and pericytes can be distinguished by SM-MHC and PDGFRβ specific antibodies. Coronary artery smooth muscle cells are positive for SM-MHC and PDGFRβ (arrows) while pericytes only stain for PDGFRβ (arrowheads). (FIG. 2D) PDGFRβ immunostaining of PDGFRα-GFP hearts demonstrate that the two markers do not significantly overlap. PDGFRβ$^+$ cells (red) wrap around the vessel (arrowhead), while PDGFRα$^+$ cells usually exist in-between vessels (asterisk). (FIG. 2E) PDGFRβ+ cells (arrowhead) are embedded within a Collagen IV$^+$ basement membrane (arrow). (FIG. 2F and FIG. 2G) PDGFRβ overlaps with NG2-DsRed labeling (FIG. 2F) and Notch3 immunostaining (FIG. 2G). (FIG. 2H) Quantification of marker expression and lineage labeling in PDGFRβ$^+$ cells in the free walls of the developing heart ventricles. The number of cells analyzed are indicated. (FIG. 2I) PDGFRβ$^+$ pericytes are the most numerous epicardial-derived cell type at the e14.5 coronary artery (CA) remodeling zone. 72% of Tbx18-Cre lineage traced cells are pericytes (PDGFRβ+) (n=14 hearts from 6 litters). The epicardial derived PDGFRβ$^-$ fraction contains mostly PDGFRα$^+$ fibroblasts. (FIG. 2J) Tbx18-Cre lineage tracing shows that the majority of caSMCs are epicardial derived. CA, coronary artery, Scale bars, A and B, 20 µm; FIG. 2C and FIG. 2D, 50 µm; FIG. 2E, 10 µm; FIG. 2F and FIG. 2G, 50 µm; J, 100 µm.

(FIG. 3A and FIG. 3B) Composition of epicardial-derived clones. (FIG. 3A) Confocal images of clones from indicated ages (e13.5, e15.5, and adult). Left panels are low magnification views of entire clones and middle panels are internal views of circled clones, which are near coronary arteries in e15.5 and adult. Boxed regions are separated channels as examples of marker expression with white showing clone label for morphology. Note that PDGFRβ staining is punctate while the clone label is uniform throughout the cell. Asterisks indicate long cellular processes in adult pericytes. Schematics of each are on the far right. (FIG. 3B) Graph showing cell types within individual clones. caSMC, coronary artery smooth muscle cell; epi, epicardial cell; peri, pericyte; Scale bars, 100 µm.

(FIG. 4C) No recombination occurs in NG2-CreER,Rosa$^{tdtomato}$ animals the absence of tamoxifen (tam). (FIG. 4D) E11.5 dosing of NG2-CreER induces lineage labeling (green) in pericytes (arrowhead), smooth muscle (boxed region), and some cardiomyocytes (arrow). (FIG. 4E) Boxed region in FIG. 4D showing lineage labeled pericytes (green, arrowheads) and coronary artery smooth muscle (yellow, arrows)(n=10 hearts from 3 litters). Endothelial cells are in blue (VE-cadherin$^+$). Right panel is boxed region in far left panel. (FIG. 4F) Labeled pericytes (arrowhead), smooth muscle (boxed region), and rare cardiomyocytes (arrow) in Notch3-CreER lineage trace. (FIG. 4G) Boxed region in F showing lineage labeled pericytes (green, arrowheads) and coronary artery smooth muscle (yellow, arrows)(n=11 hearts from 2 litters). Endothelial cells are in blue (VEGFR2+). Right panel is boxed region in far left panel. Ao, aorta; caSMC, coronary artery smooth muscle cell; epi, epicardium; r ven, right ventricle, Scale bars: FIG. 4C, FIG. 4D and FIG. 4F, 100 µm; E and G 50 µm.

(FIG. 5A) Absence of SM-MHC+ smooth muscle around coronary arteries (CA) in PDGFRβ knockout hearts. (FIG. 5B) Notch3+ mural cells (green) are decreased at the coronary artery remodeling zone (CA rz) in PDGFRβ-deficient hearts (n=8 from 4 litters). (FIG. 5C) Quantification of pericyte numbers per field of view (FOV)(wild type, n=7 hearts; mutant, n=5). Error bars are s.d.; * p≤0.05. (FIG. 5D) Schematic demonstrating the hypothesized epicardial to smooth muscle differentiation pathway and how it is affected in PDGFRβ-null mice. Greyed cells are reduced or absent. Ao, aorta; CA rz, coronary artery remodeling zone; caSMC, coronary artery smooth muscle cell; epi, epicardium; r ven, right ventricle. Scale bars: A, 100 µm; B, 50 µm.

FIG. 6A-6I. Notch3 is required for coronary artery smooth muscle development (FIG. 6A and FIG. 6B) Mural cells around coronary vessels increase Notch3 protein expression at the coronary artery remodeling zone (CA rz) while PDGFRβ levels remain the same. (FIG. 6A) Confocal image of a representative remodeling zone. (FIG. 6B) Quantification of marker expression. Error bars are s.d. (FIG. 6C and FIG. 6D) Confocal images immunostained for VE-cadherin (blue) and Jagged-1 (green). (FIG. 6C) Jagged-1 is specifically expressed in coronary arteries (CA) and the CA rz after attachment to the aorta (ao) and induction of blood flow. (FIG. 6D) Jagged-1 is expressed in coronary vessels at e13.5 soon after aortic attachment and CA stem formation, but not in Isl1 mutant littermates with delays in attachment and arterial blood flow. (FIG. 6E) Table of Jagged-1 protein expression in wild type (Wt) and Isl1 mutants. (FIG. 6F) Quantification of coronary artery smooth muscle cell (caSMC) coverage in Notch3-deficient hearts where dots are individual samples and error bars are s.d. * p≤0.05. (FIG. 6G) SM-MHC+ caSMCs (red) are significantly reduced in Notch3-null hearts although CA caliber (dotted lines) is comparable. (FIG. 6H) Pericytes (peri, green) are not significantly reduced. (FIG. 6I) Schematic demonstrating the hypothesized epicardial to smooth muscle differentiation pathway and how it is affected in the absence of Notch3. Greyed cells are reduced. Scale bars: FIG. 6A, FIG. 6C, FIG. 6D, and FIG. 6G, 100 µm; H, 50 µm.

(FIG. 7A) Whole mount confocal imaging of embryonic kidneys (outlined with dotted lines) from the indicated ages immunostained for SM-MHC and VE-cadherin. Mature smooth muscle differentiation is detected at e14. (FIG. 7B) Schematic describing lineage tracing experimental design. (FIG. 7C) e11.5 dosing of NG2-CreER, Rosa$^{tdtomato}$ animals induces labeling (green) in smooth muscle (red, arrows)(n=11 kidneys from 2 litters). Cells within the glomerulus are also labeled (arrowheads). Scale bars: 100 µm.

(FIG. 8A) Different parts of the hypothesized epicardial to caSMC pathway were dissected using the indicated experiments. (FIG. 8B) Working model for caSMC differentiation. CA, coronary artery; caSMC, coronary artery smooth muscle cell; Epi, epicardium; Peri, pericytes.

FIG. 9A-9C. Tbx18-Cre lineage tracing and clonal analysis. (FIG. 9A) Schematic of a hearts' right lateral view. This orientation was used to image the right coronary artery (RCA). (FIG. 9B) Widespread epicardial labeling (green) in Tbx18-Cre hearts containing the mTmG Cre reporter allele. (FIG. 9C) Examples of labeled clonal clusters (teal, arrowheads) in Tbx18-Cre hearts containing the MADM Cre reporter alleles. Ao, aorta; ot, outflow tract; pt, pulmonary trunk; R atria, right atria; R ven, right ventricle. Scale bars: 100 µm.

FIG. 10A-10D. PDGFRβ+ perivascular cells are adjacent to vessels and within the basement membrane. (FIG. 10A) PDGFRβ immunostaining of PDGFRα-GFP hearts demonstrates that PDGFRβ+ cells (red) are adjacent to vessels while PDGFRα+ cells (green) are interspersed. (FIG. 10B) Fluorescent intensity measurements along the white line in a show that PDGFRβ+ cells (red peaks and arrows) are closely associated with vessels (blue peaks and arrows) while PDGFRα+ cells (green peaks and arrows) frequently reside in between vessels. (FIG. 10C and FIG. 10D) Whole mount confocal microscope images of e13.5 hearts showing that PDGFRβ+ (red) perivascular cells (arrows) are embedded within a collagen IV+ basement membrane (arrowheads). Images in FIG. 10C are z-stack projections, and FIG. 10D represents a single Z plane. Scale bars: A, 50 µm; FIG. 10C and FIG. 10D, 10 µm.

FIG. 11A and FIG. 11B, 100 µm.

FIG. 12A-12B. Epicardial-derived cells at the arterial remodeling zone are largely pericytes. Confocal images of an arterial remodeling zone from a Tbx-18-Cre, tdTomato lineage traced heart immunostained for VE-cadherin, PDGFRβ+ (FIG. 12A), and PDGFRα (FIG. 12B). The majority of epicardial-derived cells are PDGFRβ+ and tightly associate with the vessel (arrowheads)(FIG. 12A) while fewer are PDGFRα+ positive cells and in between vessels (asterisks)(FIG. 12B). Note in (FIG. 12A) that PDGFRβ has a punctate distribution on perivascular cells and, unlike the lineage marker, does not uniformly label the entire cell and all of its cell processes. Quantification is shown in (FIG. 2I). Scale bars: 20 µm.

FIG. 13A-13D. Additional examples of pericyte-coronary artery smooth muscle clones and quantification of cell location and number. (FIG. 13A) Box-and-whisker plot depicting the location of cell types in e15.5 clones with respect to the epicardium [n=91, 249, 37 and 150 for epicardial cells (epi), pericytes (peri), coronary artery smooth muscle cells (caSMCs), and other cell types, respectively]. (FIG. 13B) A pericyte-caSMC clone (green) located near a coronary artery (CA)(red). Endothelial cells shown in blue. Top left: low magnification. Top middle: A deeper slice from the boxed region shows continuous sister cells with pericyte and caSMC identity. Top right: higher magnification of middle panel. Lower panels show PDGFRβ staining in pericytes from top middle panel. Schematic is on the far right. (FIG. 13C) Quantification of the number of cells contained in e15.5 Tbx18-Cre, MADM clones. (FIG. 13D) An adult pericyte-caSMC clone (green) located near a CA (red). Pericytes display long extended processes (arrowheads) along capillaries (blue). Arrows point to caSMCs.

Low magnification is left, higher magnification is middle, and separated channels of boxed regions are right. Scale bars: 100 µm.

Figure 14:
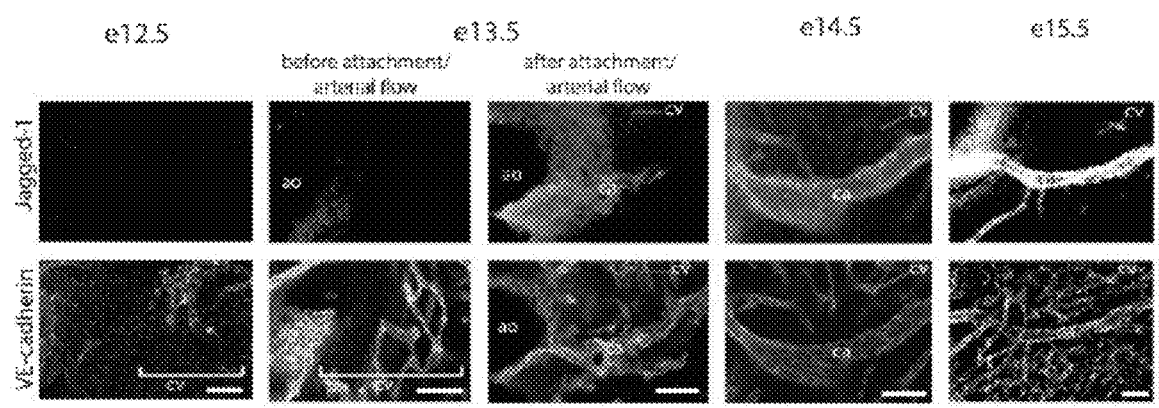

FIG. 14. Characterization of Jagged-1 expression during coronary artery development. Confocal images of VE-cadherin and Jagged-1 immunostaining in hearts from the indicated ages. Jagged-1 expression is initiated right after coronary vessels (arrowheads) connect to the aorta in the vessels directly downstream of the attachment site. Ao, aorta; ca, coronary artery; cv, coronary vessels. Scale bars: 50 µm.

Figure 15B:
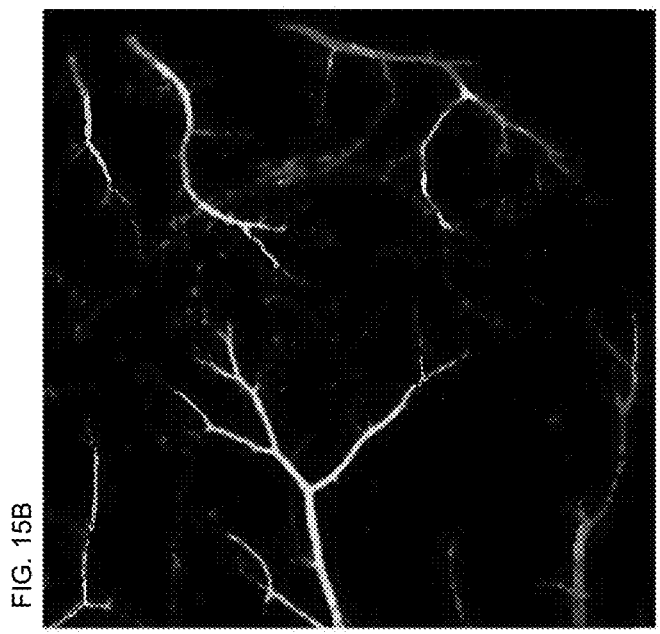
Figure 15C:
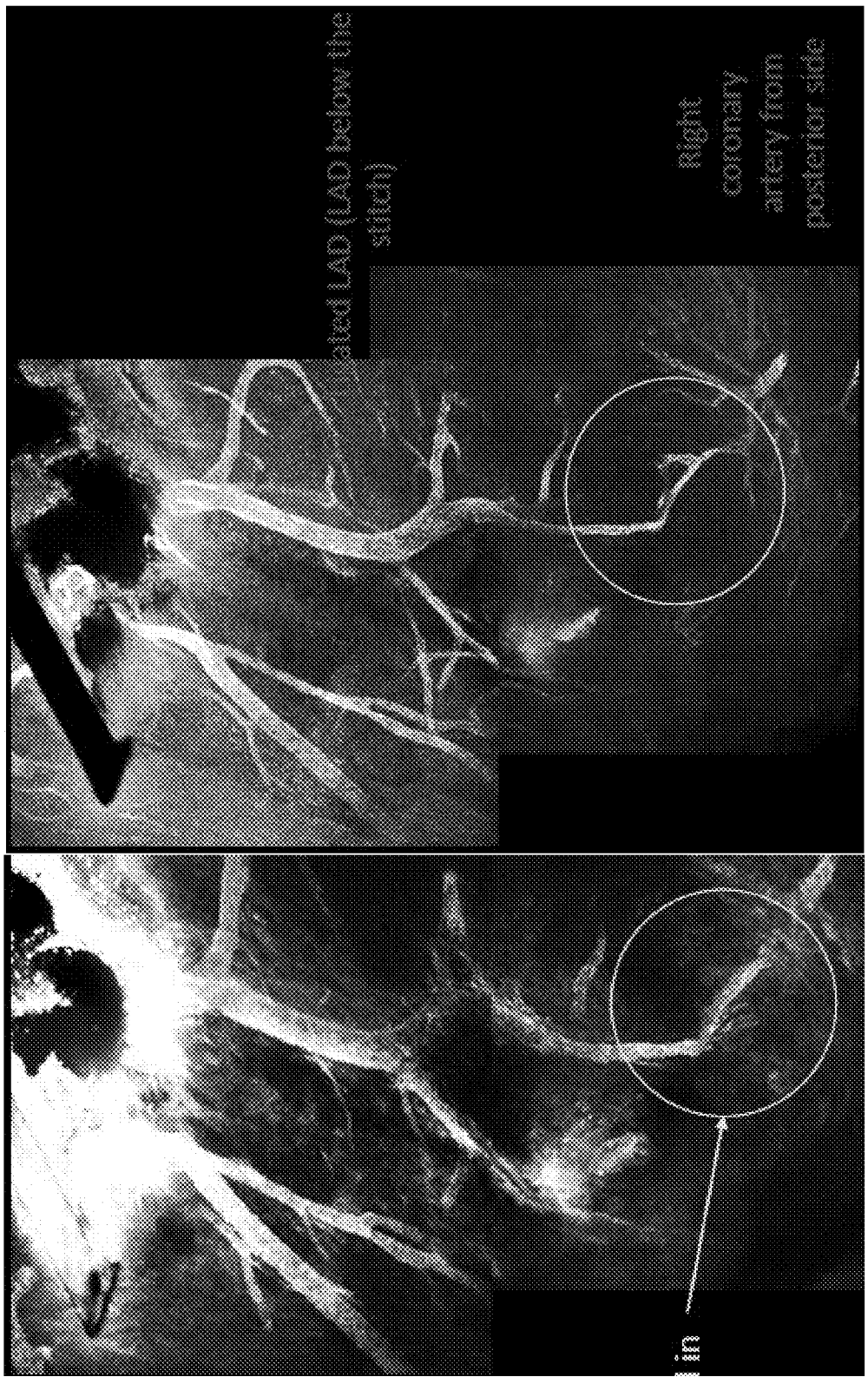

FIG. 15A-15C. Visualization of collateral artery growth. FIG. 15A Control postnatal heart stained with sma (smooth muscle marker) and connexin (Cx40 with tomato marker), and a merged image. As shown in FIG. 15B, the postnatal left and right arteries do not connect to each other. Shown in FIG. 15C, in a ligated heart model, the collateral arteries are joined.

DETAILED DESCRIPTION OF THE EMBODIMENTS

Methods are provided for treating a subject having a smooth muscle defect, deficiency or disease in vascular tissue through the administration of epicardial-derived pericytes isolated according to the methods described herein. Methods are also provided for treating a subject with tissue in need of vascularization with cellular therapy, the method comprising contacting the tissue in need of vascularization with epicardial-derived pericytes to stimulate angiogenesis. Also provided are systems, compositions, and kits for practicing the methods of the disclosure.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted as well as those in which prevention is desired.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

The terms "pluripotent progenitor cells", "pluripotent progenitors", "pluripotent stem cells", "multipotent progenitor cells" and the like, as used herein refer to cells that are capable of differentiating into two of more different cell types and proliferating. Non limiting examples of pluripotent precursor cells include but are not limited to embryonic stem cells, blastocyst derived stem cells, fetal stem cells, induced pluripotent stem cells, ectodermal derived stem cells, endodermal derived stem cells, mesodermal derived stem cells, neural crest cells, amniotic stem cells, cord blood stem cells, adult or somatic stem cells, neural stem cells, bone marrow stem cells, bone marrow stromal stem cells, hematopoietic stem cells, lymphoid progenitor cell, myeloid progenitor cell, mesenchymal stem cells, epithelial stem cells, adipose derived stem cells, skeletal muscle stem cells, muscle satellite cells, side population cells, intestinal stem cells, pancreatic stem cells, liver stem cells, hepatocyte stem cells, endothelial progenitor cells, hemangioblasts, gonadal stem cells, germline stem cells, and the like.

Pluripotent progenitor cells may be acquired from public or commercial sources or may be newly derived. As described herein, in some instances, pluripotent progenitor cells of the subject disclosure are those cells capable of giving rise to smooth muscle precursor cells and/or differentiated smooth muscle cells, including without limitation coronary artery smooth muscle. A cell may be naturally capable of giving rise to smooth muscle precursor cells and/or differentiated smooth muscle cells or may be artificially made (e.g., reprogrammed, dedifferentiated, transdifferentiated, etc.) to be capable of giving rise to smooth muscle precursor cells and/or differentiated smooth muscle cells. By "naturally capable" is meant that giving rise to smooth muscle precursor cells and/or differentiated smooth muscle cells represents part of the natural developmental lineage or the natural differentiation potential of the cell. As such, cells made capable of giving rise to smooth muscle precursor cells and/or differentiated smooth muscle cells artificially are generally cells that do not have such capability naturally.

The term "smooth muscle precursors" refers to precursor and/or progenitor cells capable of giving rise to differentiated smooth muscle and/or differentiating into smooth muscle cells either before or after engraftment into smooth muscle. The term smooth muscle precursor may refer to any cell that is restricted to the smooth muscle lineage excluding terminally differentiated smooth muscle cells. In some embodiments, smooth muscle precursors are epicardial-derived pericytes.

The term "lineage restricted", as used herein, refers to a cell that is not totipotent and has limited or defined differentiation potential. By limited or defined differentiation potential it is meant that the cell is incapable of differentiating or being differentiated into one or more particular cell types without the use of methods of dedifferentiation or transdifferentiation. Linage restricted cells may or may not be proliferative and may or may not be pluripotent, as such lineage restricted cells may be progenitor or differentiated cell types. A cell may be lineage restricted at any point in development or cellular differentiation and the lineage restriction of cells will vary widely. For example, a cell may be lineage restricted to the progeny of a particular germ layer and thus may be endoderm restricted, mesoderm restricted or ectoderm restricted. A cell may be lineage restricted to generate the progeny of a particular tissue type or cell type, e.g., cells may be smooth muscle progenitors restricted to smooth muscle cell types or progeny. Lineage restriction of a cell may be determined in a variety of ways known to the ordinary skilled artisan including but not limited to culturing the cells under various conditions to determine lineage potential, transplantation of the cells into various environments to determine lineage potential, gene or protein expression assays including transcriptomics, and proteomic assays, and the like. In some instances, a cell may be determined to be lineage restricted based on the expression of one or more lineage markers, e.g., a smooth muscle lineage marker may indicate smooth muscle lineage restriction. In some instances, a cell may be determined to be lineage restricted based on a cellular behavior that is characteristic of a one or more particular cell lineages, e.g., a smooth muscle lineage cellular behavior characteristic, or the loss of cellular behavior that is characteristic that is characteristic of a one or more particular cell type, e.g., loss of characteristic of an iPS cell or an embryonic stem cell, e.g., loss of totipotency or a morphological feature characteristic of an iPS or of an embryonic stem cell.

The term "population", e.g., "cell population" or "population of cells", as used herein means a grouping (i.e., a population) of two or more cells that are separated (i.e., isolated) from other cells and/or cell groupings. For example, a 6-well culture dish can contain 6 cell populations, each population residing in an individual well. The cells of a cell population can be, but need not be, clonal derivatives of one another. A cell population can be derived from one individual cell. For example, if individual cells are each placed in a single well of a 6-well culture dish and each cell divides one time, then the dish will contain 6 cell populations. The cells of a cell population can be, but need not be, derived from more than one cell, i.e. non-clonal. The cells from which a non-clonal cell population may be derived may be related or unrelated and include but are not limited to, e.g., cells of a particular tissue, cells of a particular sample, cells of a particular lineage, cells having a particular morphological, physical, behavioral, or other characteristic, etc. A cell population can be any desired size and contain any number of cells greater than one cell. For example, a cell population can be 2 or more, 10 or more, 100 or more, 1,000 or more, 5,000 or more, $10^4$ or more, $10^5$ or more, $10^6$ or more, $10^7$ or more, $10^8$ or more, $10^9$ or more, $10^{10}$ or more, $10^{11}$ or more, $10^{12}$ or more, $10^{13}$ or more, $10^{14}$ or more, $10^{15}$ or more, $10^{16}$ or more, $10^{17}$ or more, $10^{18}$ or more, $10^{19}$ or more, or $10^{20}$ or more cells.

The terms "homogenous population", as it relates to cell populations, refers to a cell population that is essentially pure and does not consist of a significant amount of undesired or contaminating cell types. By significant amount, in this context, is meant an amount of undesired or contaminating cell types that negatively impacts the use of the isolated desired cell population. As such, the actual amount of undesired or contaminating cells that defines a significant amount will vary and depend on the particular type of undesired or contaminating cells. For example, in a population of smooth muscle precursor cells used in the treatment of a subject, a significant amount of pre-cancerous or cancer causing contaminating cell types will be small as such cells have a high capacity to negatively impact the use of the isolated desired cell population. In comparison, e.g., in a population of smooth muscle precursor cells used in the treatment of a subject, a significant amount of contaminating differentiated smooth muscle cells may be relatively large as such cells have a low capacity to negatively impact the use of the isolated desired cell population. In some instances, a homogenous population may refer to a highly enriched population. Levels of homogeneity will vary, as described, and may, in some instances, be greater than 60% pure, including e.g., more than 65%, more than 70%, more than 75%, more than 80%, more than 85%, more than 90%, more than 95%, more than 96%, more than 97%, more than 98%, more than 99%, more than 99.5%, more than 99.6%, more than 99.7%, more than 99.8%, and more than 99.9%.

The term "heterologous", as it refers to a "heterologous sequence", means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter.

The term "autologous", as it refers to "autologously derived cells" and "autologous transplantation", means derived from the subject that is to be treated or is to receive the cells as a cellular transplant. Autologously derived cells used in an autologous transplantation need not be unaltered and, in many instances, may be modified or used to derive progeny that are ultimately used in the transplant. In some instances, modified cells or cell progeny may be referred to as autologously derived cells if the modified cells or cell progeny are used in a treatment of a subject from which cells used to derive the modified cells or cell progeny were derived.

The term "tissue" refers to a collection of cells having a similar morphology and function. In some embodiments, the tissue is smooth muscle tissue.

The term "vessels" refers to a tubular structure carrying blood through tissues and organs, such as a vein, artery, or capillary. In some embodiments, the vessels are coronary arteries.

The term "pericytes" refers to mural cells that wrap microvascular blood vessels and regulate their development and function. Pericytes share features with smooth muscle cells including close apposition to the vessel and some molecular markers, but differ in their contractile protein expression profile, cell shape, location on capillaries instead of large vessels, and discontinuous covering of the endothelium. In some embodiments, pericytes are epicardial-derived pericytes.

The term "epicardial-derived pericyte" refers to PDGFRβ$^+$Notch3$^+$NG2$^+$ vascular pericytes that are intermediate progenitors for smooth muscle in the developing heart. In some embodiments, epicardial-derived pericytes are differentiated from pluripotent stem cells. In some embodiments, epicardial-derived pericytes are isolated from mouse tissue. In some embodiments, epicardial-derived pericytes are isolated from human tissue.

Methods

Aspects of the disclosure include methods for lessening the symptoms of and/or ameliorating a vascular smooth muscle cell dysfunction or deficiency, the method comprising contacting a vessel with an isolated population of epicardial-derived pericytes in a therapeutic dose effective to treat a vascular smooth muscle cell dysfunction or deficiency. Because such methods can be used to treat an individual, such methods can also be referred to as methods of treating an individual for a smooth muscle cell dysfunction or deficiency. In some embodiments the smooth muscle cell is a coronary artery.

Treatment methods described herein include therapeutic treatments, in which the subject is inflicted prior to administration, and prophylactic treatments, in which the subject is not inflicted prior to administration. In some embodiments, the subject has an increased likelihood of becoming inflicted or is suspected of having an increased likelihood of becoming inflicted (e.g., relative to a standard, e.g., relative to the average individual, e.g., a subject may have a genetic predisposition to a smooth muscle disease or deficiency and/or a family history indicating increased risk of a smooth muscle disease or deficiency), in which case the treatment can be a prophylactic treatment. In some embodiments, the individual to be treated is an individual with a smooth muscle disease or deficiency.

As used herein the terms "a smooth muscle disease or deficiency" and "a smooth muscle cell dysfunction or deficiency" are used interchangeably and include any form of smooth muscle disease or deficiency whether acute or chronic and whether at the cellular, tissue, organ, or organism level. Such diseases, deficiencies, and dysfunctions include but are not limited to, e.g., disease or deficiency of the smooth muscle of the vascular system, disease or deficiency of the smooth muscle of the cardiovascular system, and symptoms resulting from smooth muscle disease or dysfunction including both medically relevant symptoms and cosmetic symptoms. Smooth muscle dysfunction also includes a smooth muscle disease or deficiency as a result of any other primary condition, e.g., resulting a symptom of a smooth muscle system or tissue. In some cases, the individual has recently undergone treatment for a smooth muscle disease or deficiency (e.g., corrective surgery, etc.). Any and all forms of a smooth muscle disease or deficiency, whether treated or untreated, or a smooth muscle disease or deficiency resulting from any primary condition, whether treated or untreated, are suitable conditions to be treated by the subject methods described herein.

Aspects of the disclosure also include methods for lessening the symptoms of and/or ameliorating a loss or absence of vascular tissue, the method comprising contacting a vessel with an isolated population of epicardial-derived pericytes in a therapeutic dose effective to stimulate angiogenesis.

Examples of conditions and diseases amenable to treatment according to the method of the invention related to increasing angiogenesis include any condition associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, heart attack (myocardial infarction) or other vascular death, stroke, death or loss of limbs associated with decreased blood flow, and the like.

Other forms of therapeutic angiogenesis include, but are not necessarily limited to, the use of a cell population of the invention to accelerate healing of wounds or ulcers (e.g., as a result of physical injury or disease, e.g., cutaneous ulcers, diabetic ulcers, ulcerative colitis, and the like); to improve the vascularization of skin grafts or reattached limbs so as to preserve their function and viability; to improve the healing of surgical anastomoses (e.g., as in re-connecting portions of the bowel after gastrointestinal surgery); and to improve the growth of skin or hair.

The effective dose of cells administered varies depending upon the goal of the administration, the health and physical condition of the individual to be treated, age, the taxonomic group of individual to be treated (e.g., human, non-human primate, primate, etc.), the degree of resolution desired (e.g., the amount of alleviation or reduction of symptoms), the formulation of the cell composition, the treating clinician's assessment of the medical situation, and other relevant factors.

A "therapeutically effective dose" or "therapeutic dose" is an amount sufficient to effect desired clinical results (i.e., achieve therapeutic efficacy) or reduce, alleviate, or prevent symptoms to a desired extent as determined by the patient or the clinician. A therapeutically effective dose can be administered in one or more administrations. For purposes of this disclosure, a therapeutically effective dose of cells (e.g., epicardial-derived pericytes) and/or compositions (e.g., epicardial-derived pericyte compositions) is an amount that is sufficient, when administered to (e.g., transplanted into) the individual, to palliate, ameliorate, stabilize, reverse, prevent, slow or delay the progression of the disease state (e.g., smooth muscle dysfunction, smooth muscle deficiency) by, for example, inducing stabilization, repair, or regeneration of existing smooth muscle.

In some embodiments, a therapeutically effective dose of cells (e.g., epicardial derived pericytes, etc.) is $1\times10^3$ or more cells (e.g., $5\times10^3$ or more, $1\times10^4$ cells, $5\times10^4$ or more, $1\times10^5$ or more, $5\times10^5$ or more, $1\times10^6$ or more, $2\times10^6$ or more, $5\times10^6$ or more, $1\times10^7$ cells, $5\times10^7$ or more, $1\times10^8$ or more, $5\times10^8$ or more, $1\times10^9$ or more, $5\times10^9$ or more, or $1\times10^{10}$ or more).

In some embodiments, a therapeutically effective dose of cells is in a range of from $1\times10^3$ cells to $1\times10^{10}$ cells (e.g, from $5\times10^3$ cells to $1\times10^{10}$ cells, from $1\times10^4$ cells to $1\times10^{10}$ cells, from $5\times10^4$ cells to $1\times10^{10}$ cells, from $1\times10^5$ cells to $1\times10^{10}$ cells, from $5\times10^5$ cells to $1\times10^{10}$ cells, from $1\times10^6$ cells to $1\times10^{10}$ cells, from $5\times10^6$ cells to $1\times10^{10}$ cells, from $1\times10^7$ cells to $1\times10^{10}$ cells, from $5\times10^7$ cells to $1\times10^{10}$ cells, from $1\times10^8$ cells to $1\times10^{10}$ cells, from $5\times10^8$ cells to $1\times10^{10}$, from $5\times10^3$ cells to $5\times10^9$ cells, from $1\times10^4$ cells to $5\times10^9$ cells, from $5\times10^4$ cells to $5\times10^9$ cells, from $1\times10^5$ cells to $5\times10^9$ cells, from $5\times10^5$ cells to $5\times10^9$ cells, from $1\times10^6$ cells to $5\times10^9$ cells, from $5\times10^6$ cells to $5\times10^9$ cells, from $1\times10^7$ cells to $5\times10^9$ cells, from $5\times10^7$ cells to $5\times10^9$ cells, from $1\times10^8$ cells to $5\times10^9$ cells, from $5\times10^8$ cells to $5\times10^9$, from $5\times10^3$ cells to $1\times10^9$ cells, from $1\times10^4$ cells to $1\times10^9$ cells, from $5\times10^4$ cells to $1\times10^9$ cells, from $1\times10^5$ cells to $1\times10^9$ cells, from $5\times10^5$ cells to $1\times10^9$ cells, from $1\times10^6$ cells to $1\times10^9$ cells, from $5\times10^6$ cells to $1\times10^9$ cells, from $1\times10^7$ cells to $1\times10^9$ cells, from $5\times10^7$ cells to $1\times10^9$ cells, from $1\times10^8$ cells to $1\times10^9$ cells, from $5\times10^8$ cells to $1\times10^9$, from $5\times10^3$ cells to $5\times10^8$ cells, from $1\times10^4$ cells to $5\times10^8$ cells, from $5\times10^4$ cells to $5\times10^8$ cells, from $1\times10^5$ cells to $5\times10^8$ cells, from $5\times10^5$ cells to $5\times10^8$ cells, from $1\times10^6$ cells to $5\times10^8$ cells, from $5\times10^6$ cells to $5\times10^8$ cells, from $1\times10^7$ cells to $5\times10^8$ cells, from $5\times10^7$ cells to $5\times10^8$ cells, or from $1\times10^8$ cells to $5\times10^8$ cells).

In some embodiments, the concentration of cells (e.g., isolated epicardial derived pericytes, etc.) to be administered is in a range of from $1\times10^5$ cells/ml to $1\times10^9$ cells/ml (e.g., from $1\times10^5$ cells/ml to $1\times10^8$ cells/ml, from $5\times10^5$ cells/ml to $1\times10^8$ cells/ml, from $5\times10^5$ cells/ml to $5\times10^7$ cells/ml, from $1\times10^6$ cells/ml to $1\times10^8$ cells/ml, from $1\times10^6$ cells/ml to $5\times10^7$ cells/ml, from $1\times10^6$ cells/ml to $1\times10^7$ cells/ml, from $1\times10^6$ cells/ml to $6\times10^6$ cells/ml, or from $2\times10^6$ cells/ml to $8\times10^6$ cells/ml).

In some embodiments, the concentration of cells to be administered is $1\times10^5$ cells/ml or more (e.g., $1\times10^5$ cells/ml or more, $2\times10^5$ cells/ml or more, $3\times10^5$ cells/ml or more, $4\times10^5$ cells/ml or more, $5\times10^5$ cells/ml or more, $6\times10^5$ cells/ml or more, $7\times10^5$ cells/ml or more, $8\times10^5$ cells/ml or more, $9\times10^5$ cells/ml or more, $1\times10^6$ cells/ml or more, $2\times10^6$ cells/ml or more, $3\times10^6$ cells/ml or more, $4\times10^6$ cells/ml or more, $5\times10^6$ cells/ml or more, $6\times10^6$ cells/ml or more, $7\times10^6$ cells/ml or more, or $8\times10^6$ cells/ml or more).

In some instances, an effective dose of the cells described herein may be co-administered with one or more additional agents. For example, an effective dose of epicardial-derived pericytes from a homogenous population may be co-administered with one or more additional agents. Additional agents useful in such co-administration include agents that improve the overall effectiveness of the effective dose of cells or decrease the dose of cells necessary to achieve an effect essentially equal to administration of an effective dose of the cells without the additional agent. Non-limiting examples of additional agents that may be co-administered with smooth muscle precursors derived according to the methods described herein include: differentiated smooth muscle cells, conventional agents, non-smooth muscle progenitor cells, pro-survival factors, pro-engraftment factors, functional mobilization agents, and the like. By pro-survival factors is meant a factor or agent that may be added to the medium, culture media, delivery excipient, or storage solution that promotes the survival of a desired cell type. Such pro-survival factors may be general pro-survival factors that generally promote the survival of most cell types or may be specific pro-survival factors that only promote the survival of certain specific cell types. In some instances, pro-survival factors of the subject disclosure include but are not limited to, e.g., Rho-associated kinase (ROCK) inhibitor, pinacidil, allopurinol, uricase, cyclosporine (e.g., low does, i.e., sub-immunosuppressive dose, cyclosporine), ZVAD-fmk, pro-survival cytokines (e.g., insulin-like growth factor-1 (IGF-1)), extra cellular matrix (ECM) components, hydrogels, matrigel, collagen, gelatin, agarose, alginate, poly(ethylene glycol), hyaluronic acid, etc.

By pro-engraftment factors is meant a factor or agent that may be added to the administered dose or the delivery excipient or the cell storage solution that, upon delivery of the cells into a subject for treatment, increase the engraftment of the administered cells into the tissue targeted for engraftment and therapy. In some instances, pro-engraftment factors include factors that physically retain the administered cells at the delivery site, e.g., the injection site in the case of direct injection to the affected area, including but not limited to, e.g., gels, polymers, and highly viscous liquids that have physical properties that prevent the administered cells from freely diffusing. Such gels, polymers, and highly viscous liquids include but are not limited to e.g., ECM components, hydrogels, matrigel, collagen, gelatin, agarose, alginate, poly(ethylene glycol), and the like.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The cells may be introduced by injection, catheter, intravenous perfusion, or the like. The cells may be frozen at liquid nitrogen temperatures and stored for long periods of time, being capable of use upon thawing. Once thawed, the cells may be expanded by use of growth factors and/or feeder cells or in feeder-free conditions associated with progenitor cell proliferation and differentiation. In some instances, the cells may be administered fresh such that the cells are expanded and differentiated and administer without being frozen.

The cells (e.g., epicardial-derived pericytes, etc.) and/or compositions (epicardial-derived pericyte compositions) of this disclosure can be supplied in the form of a pharmaceutical composition, comprising an isotonic excipient or buffer or media prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells of the subject methods (e.g., epicardial-derived pericytes) may be autologously derived. By autologously derived it is meant that the cells are derived from the subject that is to be treated with the cells. The cells may be derived from a tissue sample obtained from the subject. In some instances, the sample from which cells are derived may be a biopsy or swab, e.g., a biopsy or swab collected to diagnose, monitor, or otherwise evaluate the subject, e.g., diagnose the subject for a smooth muscle dysfunction or deficiency, or for cell collection. In some instances, the autologous sample from which the cells are derived may be a previously collected and stored sample, e.g., a banked tissue sample, from the subject to be treated, including but not limited to e.g., banked cardiac tissue or cells, banked vascular tissue or cells, banked umbilical cord blood tissue or cells, and the like.

In some instances, cells of the subject methods (e.g., epicardial-derived pericytes) may be non-autologously derived. By non-autologously derived it is meant that the cells are not derived from the subject that is to be treated with the cells. In some instances, non-autologously derived cells may be xeno-derived (i.e., derived from a non-human animal) or allo-derived (i.e. derived from a human donor other than the subject to be treated). Non-autologously derived cells or tissue may be derived from any convenient source of cells or tissue collected by any convenient means.

Whether to use autologously derived or non-autologously derived cells may be determined according to the discretion of the subject's clinician and may depend on, e.g., the health, age, genetic predisposition or other physical state of the subject. In some instances, autologous cells may be preferred, including, e.g., to decrease the risk or immune rejection of the transplanted cells. In some instances, non-autologous cells may be preferred, including, e.g., when the subject has a genetic defect that affects smooth muscle production.

In some instances, the epicardial-derived pericyte cells used according to the methods described herein may be genetically unmodified. By "genetically unmodified" is meant that essentially no modification of the genome of the cells transplanted into the subject has been performed. Encompassed within the term genetically unmodified are instances wherein transient genetic modification is performed at some point during the derivation of the cells but essentially no genetic modification persists in the cells that are eventually transplanted into the subject (i.e. the cells are essentially indistinguishable before the transient genetic modification and after the course of the transient modification). Also encompassed within the term genetically unmodified are instances wherein the genome of the cells is not transiently or stably modified, e.g., where the cells are manipulated, e.g., pluripotent progenitors are derived or cells are transformed, without genetic modification (e.g., modification of the nucleotide sequence of the genome) of the cells.

In some instances, the cells (e.g., epicardial-derived pericytes) used according to the methods described herein may be genetically modified. By "genetically modified" is meant that at least one nucleotide is added to, changed within, or deleted from of the genome of the cell. In some instances, the genetic modification may be an insertion of a heterologous sequence, e.g., a sequence that encodes a tag, a label sequence, a reporter, a selectable marker, a gene encoding a protein from a species different from that of the host cell, etc. In some instances, the genetic modification corrects a defect or a mutation within the cell, e.g., corrects an anomalous mutation that confers a smooth muscle cell dysfunction or deficiency. In some instances, the genetic modification deletes or renders inoperable an endogenous gene of the host cell. In some instances, the genetic modification enhances an endogenous gene of the host cell. In some instances, the genetic modification represents a change that enhances survival, control of proliferation, and the like. Cells may be genetically altered by transfection or transduction with a suitable vector, homologous recombination, or other appropriate technique, so that they express a heterologous sequence or have altered expression of an endogenous gene.

Aspects of the disclosure include methods of removing and/or isolating identified cells in order to generate a homogenous population of a desired cell type, e.g., a homogenous population of epicardial-derived pericytes. In some instances a homogenous population of a desired cell type may be achieved through the removal and collection (i.e. isolation) of essentially only the desired cell type. Methods of cell removal useful in the methods described herein include but are not limited to, e.g., microfluidic cell extraction, laser cell extraction, laser cell ablation, laser microdissection, ultra-sonic cell ablation, chemical dissociation, or enzymatic dissociation, physical dissociation, etc. In some instances, aberrant cells are removed without disturbing the remaining culture or without disturbing desired cell types. In some instances, cells are removed through removal of the substrate on which the cells are adhered, e.g., a tissue culture substrate or an element of a tissue culture substrate array as described herein.

Aspects of the disclosure include methods of collecting a homogenous population of desired cells, e.g., for the preparation of a cell therapy or pharmacological composition to be used in the therapeutic methods described herein. In some instances, collecting of a homogenous population of desired cells, e.g., a homogenous population of epicardial-derived pericytes, is achieved by dissociating and collecting essentially all of the cells of a homogenous culture of desired cells, e.g., a culture of cells derived from a pluripotent progenitor cell, an epicardial tissue sample, etc. In some instances, collecting of a homogenous population of desired cells is achieved by selectively dissociating the desired cells, e.g., using the methods described herein for identifying cell types and selectively dissociating identified cells, and collecting only the dissociated cells while leaving the undesired cells attached to the culture vessel. Following dissociation of a homogenous population of desired cells conventional methods of concentrating and/or isolating the cells may be optionally employed, including but not limited to, e.g., centrifugation, FACS sorting, magnetic cell sorting, filtering, re-culturing, and the like, and combinations thereof. FACS sorting may be performed to select for cells derived from epicardial tissue that positively one or more of NG2, Notch3 and PDGFRβ. For example, the cell population may be contacted with an antibody that specifically binds one or more of NG2, Notch3 or PDGFRβ, where the antibody is detectably labeled or contacted with a second antibody that is detectable labeled; and selected by flow cytometry for cells that bear the detectable label, as known in the art.

For further elaboration of general techniques useful in the practice of this disclosure, the practitioner can refer to standard textbooks and reviews in cell biology, tissue culture, and embryology. With respect to tissue culture and stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

Compositions and Kits

Also provided are compositions and kits for use in the subject methods. The subject compositions and kits include any combination of components for performing the subject methods. In some embodiments, a composition can include, but is not limited to and does not require, the following: cell dissociation agents and/or media, cell reprogramming agents and/or media, pluripotent progenitor cells, cell culture agents and/or media, cell differentiation agents and/or media; lineage restriction agents and/or media; differentiated smooth muscle cells, conventional agents for treating incontinence, non-smooth muscle progenitor cells, pro-survival factors, pro-engraftment factors, functional mobilization agents and any combination thereof.

In some embodiments, a kit can include, but is not limited to and does not require, the following: any of the above described composition components, a sample collection container, a sample collection device (e.g., a sample collection container that includes a sample enrichment mechanism including, e.g., a filter), a tissue collection device (e.g., a biopsy device), a tissue dissociation device, a cell culture vessel, a cell production system; and any combination thereof.

In some embodiments, a kit can include, but is not limited to and does not require, a cell delivery system and/or a cell injection system configured for delivery of cells derived according to the methods described herein. For example, a kit may include a cell injection system configured for injection of delivery of cells into a desired area of the subject in order to effectively treat the subject for a smooth muscle cell dysfunction or deficiency. Such kits may include a cell delivery or injection system, as described herein, including individual components of such systems in assembled or unassembled form. In some instances, cells derived according to the methods described herein may be "preloaded" into a cell injection or delivery system such that the system is provided in a "ready-to-use" configuration. In other instances, a cell injection or delivery system may be provided in an "unloaded" configuration such that cells derived according to the methods described herein must be loaded into the system, with any desired carrier or vehicle, prior to use.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (ph; seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM); millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1: Pericytes are Progenitors for Coronary Artery Smooth Muscle

Epicardial cells on the heart's surface give rise to coronary artery smooth muscle cells (caSMCs) located deep in the myocardium. However, the differentiation steps between epicardial cells and caSMCs are unknown as are the final maturation signals at coronary arteries. Here, we use clonal analysis and lineage tracing to show that caSMCs derive from pericytes, mural cells associated with microvessels, and that these cells are present in adults. During development following the onset of blood flow, pericytes at arterial remodeling sites upregulate Notch3 while endothelial cells express Jagged-1. Deletion of Notch3 disrupts caSMC differentiation. Our data show that epicardial-derived pericytes populate the entire coronary microvasculature, but differentiate into caSMCs at arterial remodeling zones in response to blood flow-induced Notch signaling. Our data is the first demonstration that pericytes are progenitors for smooth muscle, and their presence in adult hearts reveal a new potential cell type for targeting during cardiovascular disease.

Coronary artery disease is the leading cause of death worldwide, but there is currently no effective method to regenerate new coronary arteries (CA) in diseased or injured hearts (Rubanyi G M, 2013). This is likely due to our limited understanding of CA progenitor cells and the signaling pathways that activate their differentiation. CAs are the vessels that supply blood to ventricular heart muscle and are composed of an inner endothelial cell lining wrapped by a smooth muscle covering. Coronary artery smooth muscle cells (caSMC) are particularly important due to their role in the pathogenesis of coronary artery disease. However, caSMC development, both normally during embryogenesis and ectopically during coronary artery disease, is a poorly understood process.

CaSMC development occurs during arterialization of immature coronary plexus vessels. In the murine heart, coronary endothelial cells derived primarily from the sinus venosus and endocardial cells that sprout onto the heart to form an early vascular plexus (Kattan et al., 2004, Chen et al., 2014b; Red-Horse et al., 2010; Tian et al., 2013; Wu et al., 2012). A subset of the plexus vessels differentiates into arteries once the network attaches to the aorta and begins receiving blood flow (Chen et al, 2014a, Hood et al., 1992, Peeters et al., 1997). Although ultimately adjacent to CA endothelial cells, the source of caSMCs is different. These cells arise from the mesothelial covering of the heart called the epicardium (Cai et al., 2008b; Mikawa and Gourdie, 1996; Wilm et al., 2005; Zhou et al., 2008). In rodents, caSMCs reside deep within the myocardium while epicardial cells are located on the outermost layer of the heart. During embryonic development, many epicardial cells undergo an epithelial-to-mesenchymal transition (EMT) and migrate into the deeper layers of the myocardium to form the stromal cells of the heart, including cardiac fibroblasts and caSMCs. Inhibition of epicardial migration from the surface by deletion of Platelet Derived Growth Factor Receptor β (PDGFRβ) diminishes caSMC development (Mellgreen et al., 2008; Smith et al., 2010). However, the migrating epicardial-derived cell type fated to become caSMCs has not been discovered, and the mechanisms that trigger this intermediate progenitor to differentiate into caSMCs are unknown.

Smooth muscle within other internal organs, including vascular smooth muscle, also arises from an outer mesothelial covering. Lineage tracing Mesothelin (Msln)-positive mesothelial cells and their prospective isolation and transplantation has shown that many of the abdominal and thoracic organs derive their smooth muscle and fibroblasts from the surface serosa layer (Rinkevich et al., 2012). Mesothelial to vascular smooth muscle differentiation occurred almost exclusively during developmental and early postnatal stages, but, similar to the heart, the cellular pathway bridging the surface to internal arteries has not been identified. Epicardial mesothelium of the heart also has a developmental restriction. Most migrating caSMC progenitors leave the heart surface before embryonic day 12.5 and are no longer able to migrate into the adult heart, either normally or following myocardial infarction (Wei et al., 2015; Zhou et al., 2011). However, since this time point is long before caSMCs appear, it is unclear what cell type resides in the heart to eventually receive signals to become new smooth muscle around forming arteries and whether this cell type persists in the adult. The discovery of such an intermediate progenitor could identify a cell type that could aid collateral artery formation during disease.

Here, we find that PDGFRβ$^+$Notch3$^+$NG2$^+$ vascular pericytes are intermediate progenitors for smooth muscle in the developing heart. Pericytes are mural cells that wrap microvascular blood vessels and regulate their development and function. Pericytes share features with smooth muscle cells including close apposition to the vessel and some molecular markers, but differ in their contractile protein expression profile, cell shape, location on capillaries instead of large vessels, and discontinuous covering of the endothelium. We show that pericytes lining the coronary vascular plexus respond to blood flow induced Notch3 signaling at arterial remodeling zones to become caSMCs during embryonic development. We also observed caSMC related pericytes in the adult heart presenting the possibility that the Notch3 pathway, or other arterial flow induced signal, could be manipulated in pericytes of the injured heart to participate in CA regeneration.

Results

CaSMC Development.

Figure 1E:
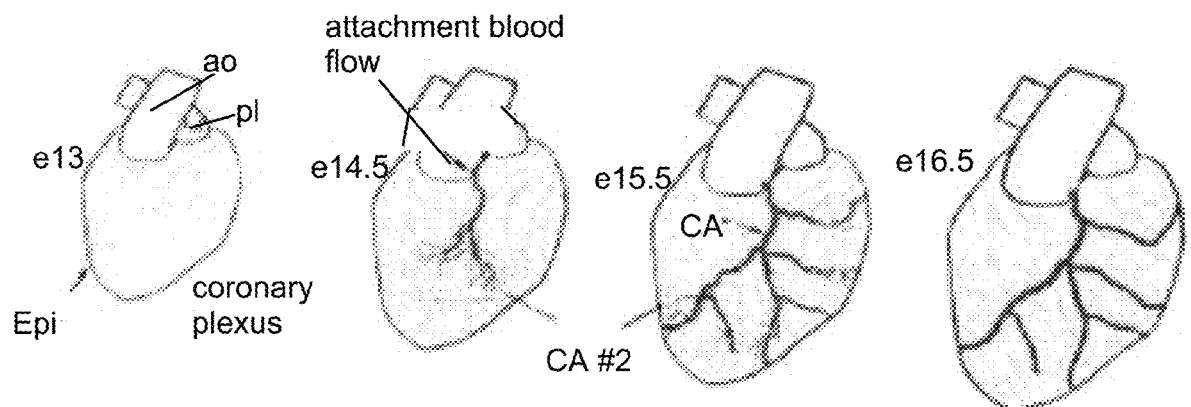

To identify where an epicardial-derived caSMC progenitor would be found, we determined where caSMCs first appear. CA development was followed using confocal imaging of intact mouse hearts immunostained for vascular endothelial-cadherin (VE-cadherin) and smooth muscle-myosin heavy chain (SM-MHC), one of the most specific markers for mature smooth muscle. Hearts are shown on the right lateral side to most effectively display developing CAs (FIG. 9A). Development of CAs begins with the invasion of VE-cadherin$^+$ endothelial cells that form an immature coronary vascular plexus, which is initially devoid of blood flow (FIG. 1A-A'''). At embryonic day (e) 13.5, the plexus vessels attach to the aorta and begin to receive blood flow. Subsequently, vascular remodeling, or fusion and enlargement of plexus vessels, is observed directly downstream of the aortic attachment site where future arteries will form. SM-MHC protein expression was first observed at e14.5 in plexus vessels that had begun to remodel into arteries (FIG. 1B-B'''). At e14.5 smooth muscle coverage was patchy and consisted of cells with both low and high SM-MHC (SM-MHC$^{low}$ or SM-MHC$^{high}$) protein expression (fluorescence measured from single confocal z-planes)(FIG. 1B'''). As this initial remodeling zone transitioned into recognizable arterial vessels at e15.5, caSMC coverage increased and most cells were SM-MHC$^{high}$ (FIG. 1C-C'''). Remodeling zones with patchy SM-MHC$^{low}$ cells were now just distal to the more mature vessels (FIG. 1C'''). These distal remodeling zones eventually transformed into mature vessels in the next developmental stage at e16.5 (FIG. 1DD'''). These data identify when and where SM-MHC$^+$ caSMCs differentiate within the context of the whole heart at single-cell resolution (FIG. 1E).

Figure 1F:
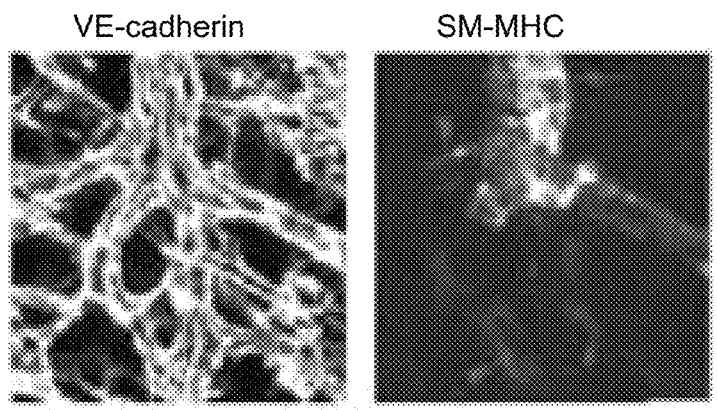
Figure 1G:
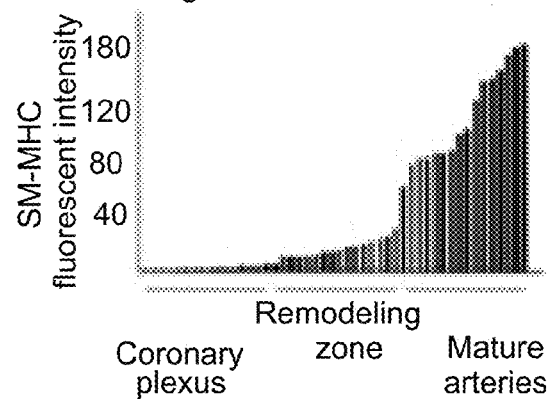
Figure 1H:
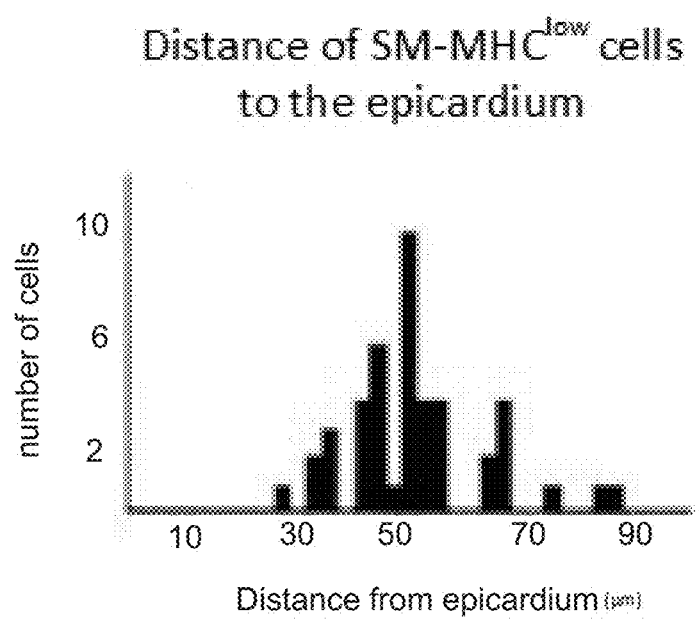
Figure 1I:
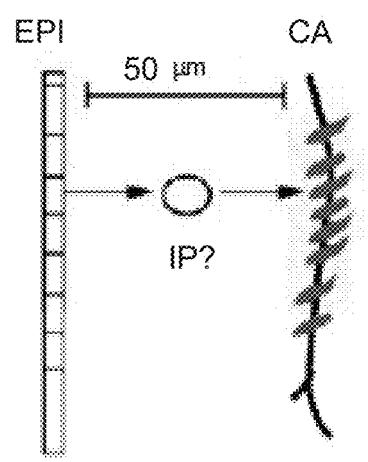

The temporal appearance and location, i.e. at the remodeling zone early in arterial development, of SM-MHC$^{low}$ cells suggested that they have recently initiated caSMC differentiation while cells expressing higher SM-MHC levels were more mature (FIG. 1F,G). Measuring the distance between SM-MHC$^{low}$ cells and the epicardium revealed that they were not on the surface of the heart, but 145 on average 50 μm deep (FIG. 1H). Thus, a putative intermediate progenitor would need to migrate through approximately 7 cell layers between the epicardium and nascent CAs where they first express the mature smooth muscle cell marker (FIG. 1I).

Clonal Analysis of Epicardial-Derived Cells.

Because most caSMCs derive from the epicardium, we aimed to find the epicardial-derived progenitor that eventually differentiates into caSMCs. Epicardial-driven Cre-expressing mice for lineage tracing exist; however, these constructs label all the other epicardial-derived stromal cells in the heart in addition to caSMCs. We needed to study the smooth muscle lineage in isolation, which is done most accurately using clonal level labeling where single cells and all their progeny are genetically marked with a fluorescent tag. Our approach was to identify caSMC progenitors by analyzing fluorescently labeled sister cells within clonal clusters that also contain caSMCs. To produce clones, epicardial cells were sparsely labeled using T-box 18 (Tbx18)-Cre (Cai et al., 2008b) coupled with the Mosaic Analysis with Double Markers (MADM) Cre reporter system. Tbx18-Cre was selected because, in control experiments with other Cre reporters, recombination was induced in the large majority of epicardial cells (FIG. 9B). The MADM system fluorescently labels Cre-expressing cells through a rare interchromosomal recombination event such that, when coupled with Tbx18-Cre, hearts contained isolated clusters of fluorescently labeled cells (FIG. 9C). We analyzed tightly associated clusters (at least 100 µm from any other labeled cell) that contained epicardium, caSMCs, and other clonally related cells, the latter of which could be the progenitor population.

Initial experiments analyzing Tbx18-Cre, MADM clones based on cellular morphology and location revealed that clones containing epicardial cells and caSMCs always contained sister cells with long, thread-like processes that wrapped around coronary vessels (FIG. 2A). This was in contrast to sister cells from clones that were adjacent to, but did not incorporate into, the caSMC layer, which were mostly located in the space between vessels instead of wrapping around them (FIG. 2B). The morphology of the caSMC-associated sister cells was characteristic of vascular pericytes, which are mural cells that tightly associate with small blood vessels and regulate their development and function (Armulik et al., 2011). To investigate the presence of pericytes in caSMC clones, we validated the use of a set of markers that would allow us to identify pericytes and caSMCs in the developing heart. These were then used to analyze an additional set of clones. The following describes our marker selection criteria.

Figures 11A, 11B:
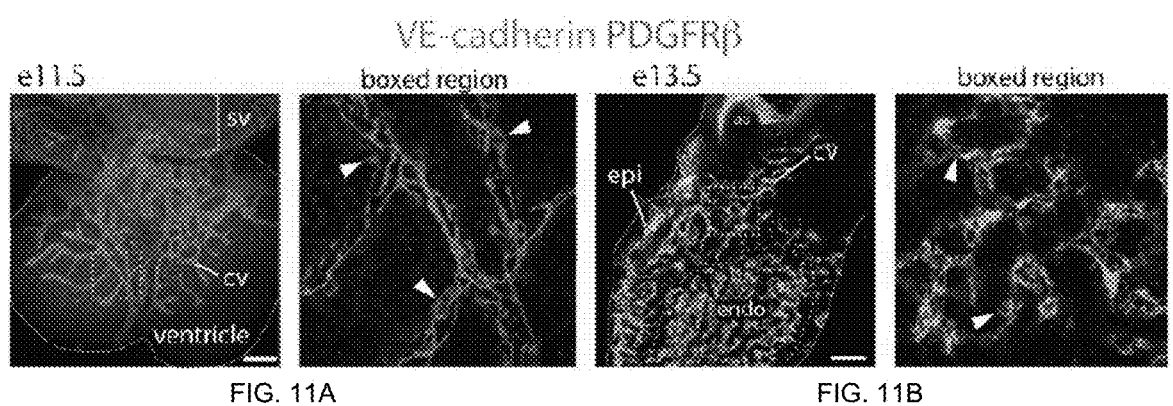
FIG. 11A-11B. Characterization of PDGFRβ+ perivascular cells in the developing heart. (A and B) PDGFRβ+ pericytes co-develop with coronary vessels (cv). Dorsal view of the e11.5 heart (FIG. 11A) and right lateral view at e13.5 (FIG. 11B) showing CVs (teal) with associated pericytes (red, arrowheads). Right panels are boxed regions. Solid lines outline the heart. Ao, aorta; CA, coronary artery; epi, epicardium; endo, endocardium; sv, sinus venosus. Scale bars.

We found that whole mount immunostaining with PDGFRβ and SM-MHC distinguished between pericytes and caSMCs. CaSMCs were positive for SM-MHC and PDGFRβ and were around mature and developing arteries (FIG. 2C). Pericytes were positive for PDGFRβ, but negative for SM-MHC (FIG. 2C). To confirm the use of PDGFRβ as a valid marker for cardiac pericytes, we further characterized PDGFRβ$^+$ perivascular cells in the developing heart. Whole mount immunohistochemistry showed that PDGFRβ$^+$ cells in the free walls of the developing heart ventricles were always closely apposed to coronary vessels in contrast to PDGFRα$^+$ fibroblasts, which were dispersed between the endothelium (FIG. 2D and FIG. 10 A,B). PDGFRβ$^+$ cells were also embedded within a Collagen IV-containing basement membrane (FIG. 2E and FIG. 10C, D). These are critical attributes for pericyte identification. They also all expressed the pericyte markers NG2 (FIG. 2F) and Notch3 (FIG. 2G). See FIG. 2H for quantification. PDGFRβ$^+$ cells were observed on the earliest coronary sprouts when the vessels first migrate directly beneath the epicardium (FIG. 11A,B). At the arterial remodeling zone where caSMCs first differentiate, 98±% of PDGFRβ+ cells were Tbx18-Cre lineage labeled consistent with most arising from the epicardium (FIG. 2H). In addition, PDGFRβ$^+$ cells were the most numerous Tbx18-Cre traced cell type in this location (FIG. 2I and FIG. 12A). The remaining 28% were predominately fibroblasts as defined by their expression of PDGFRα and variable proximity to the vessels (FIG. 2I and FIG. 12B). At time points after arteries are formed, much of the coronary smooth muscle was also lineage labeled with Tbx18-Cre (FIG. 2J) in line with other studies showing an epicardial origin for these cells. The epicardium is not thought to give rise to cells of the hematopoietic lineage, and, accordingly, PDGFRβ$^+$ cells did not overlap with CD45 staining. In summary, given their marker expression, localization within the tissue, and cellular morphology, we defined PDGFRβ+ cells to be cardiac pericytes of the developing coronary vasculature. We also show that they are the most common epicardially-derived cell type at the arterial remodeling zone making them a prime candidate for caSMC progenitors.

Figure 3A:
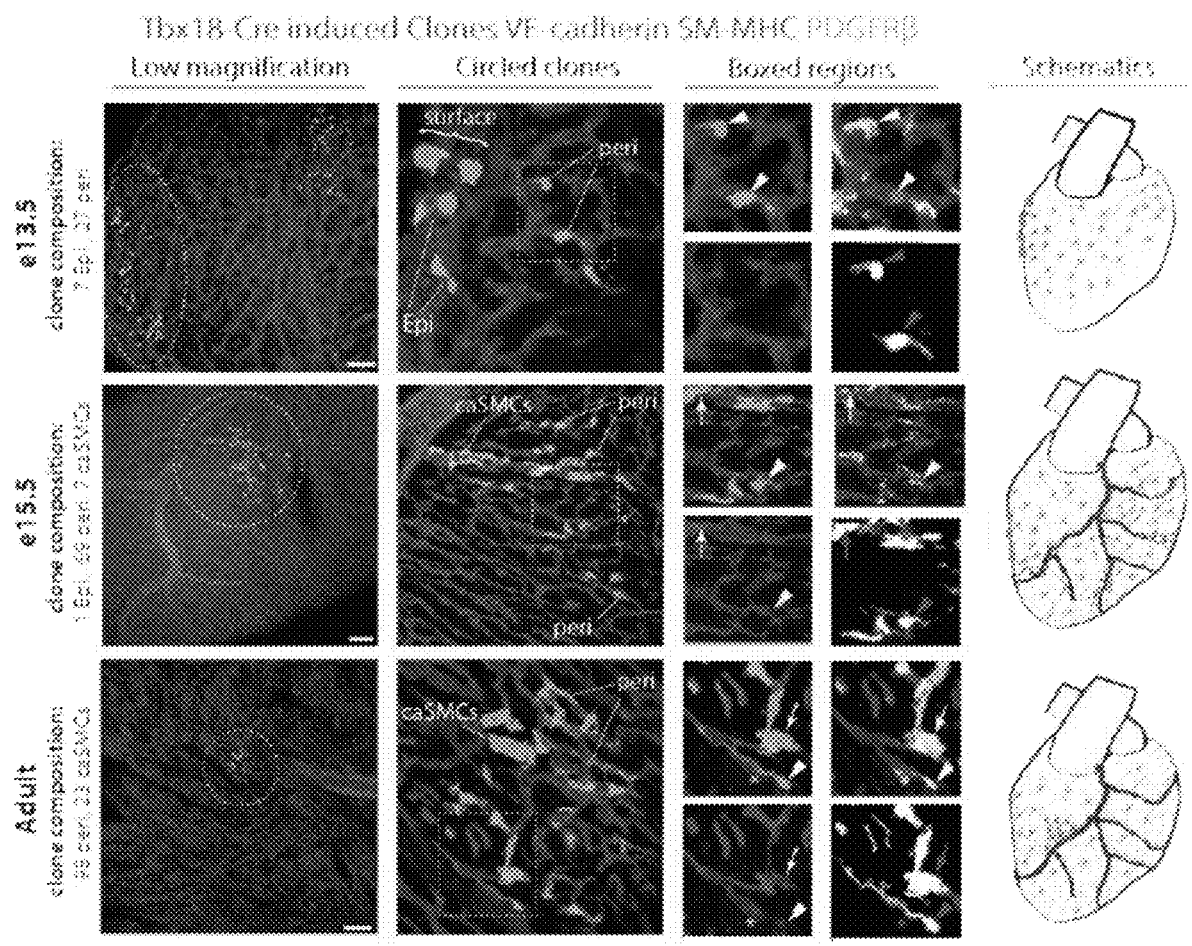
FIG. 3A-3B. Coronary artery smooth muscle cells and pericytes are clonally related.

We next used PDGFRβ and SM-MHC to analyze Tbx18-Cre-derived clonal cell clusters isolated at e13.5 and 15.5, before and after caSMCs develop, respectively. This analysis revealed a clonal and spatial relationship between caSMCs and pericytes. At e13.5 before caSMCs are present, we obtained clones consisting of just epicardial cells and pericytes, the latter of which were always located directly beneath epicardial sister cells (FIG. 3A-e13.5,B). At e15.5, clones with caSMCs always contained pericytes that filled the region of the myocardium between the epicardium and smooth muscle and were continuous with, and often touching, related caSMCs (FIG. 3A-e15.5,B, FIG. 13A,B). As expected from the Tbx18-Cre lineage trace data (FIG. 2I), pericytes were the most numerous cell type in these clones (FIG. 13C). Tbx18-Cre labels cardiomycetes, but these cells never appeared in clonal clusters with pericytes or smooth muscle. Together, the temporal sequence and spatial arrangement of Tbx18-Cre-derived clones suggested that pericytes are the intermediate differentiation step between epicardium and caSMCs.

Figure 3B:
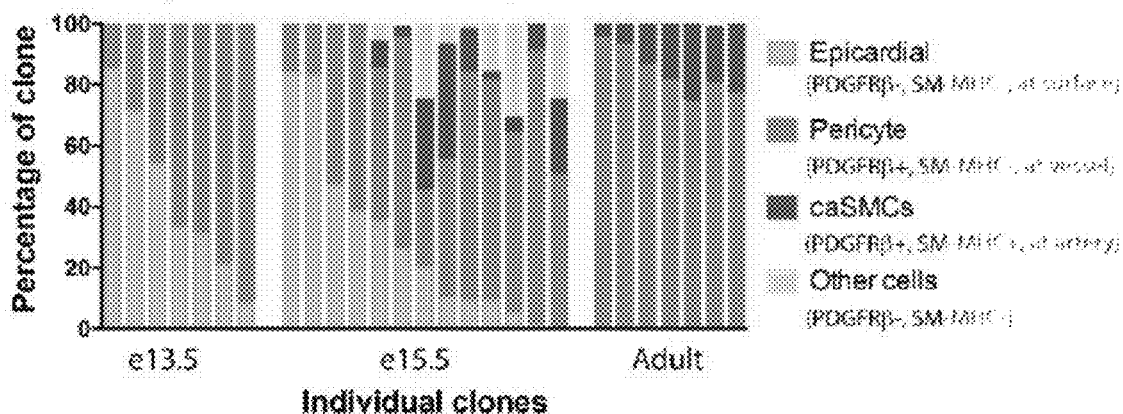

We next tested whether the pericytes that were clonally related to caSMCs during embryogenesis persisted into adulthood or were depleted after development. Strikingly, adult Tbx18-Cre, MADM hearts frequently contained tightly packed clusters of lineage labeled cells consisting of pericytes and caSMCs (FIG. 3A-adult)(n=20). Pericytes at this stage exhibited even longer, thinner processes that tracked along the vessels for greater than 5-10 times the length of their cell bodies (FIG. 3A-adult and FIG. 13D). The fact that these cells were not dispersed, even five weeks after labeling, shows that pericytes and caSMCs do not migrate significantly once their positions are established during development. In addition, our analysis indicates that pericytes around capillaries that are clonally related to caSMCs remain and function as cardiac pericytes in the adult heart (FIG. 3B). In total, our clonal analysis suggests that epicardial-derived pericytes surround the entire coronary plexus during embryonic development, but that these cells differentiate into caSMCs if located around vessels that enlarge to become arteries during remodeling. These pericytes also surround capillaries in the adult heart and could potentially become new caSMC if arterial remodeling were induced at this stage.

Lineage Tracing Pericytes in the Developing Heart.

Figure 4A:
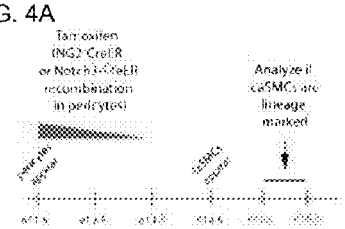
FIG. 4A-4G. Pericytes differentiate into coronary artery smooth muscle (FIG. 4A and FIG. 4B) Schematics describing the experimental design for cardiac pericyte lineage tracing (FIG. 4A) and part of the differentiation pathway being interrogated (FIG. 4B).
Figure 4B:
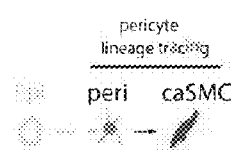
Figure 4C:
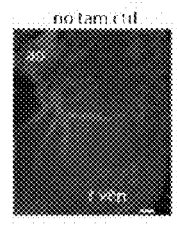
Figure 4D:
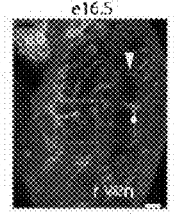
Figure 4E:
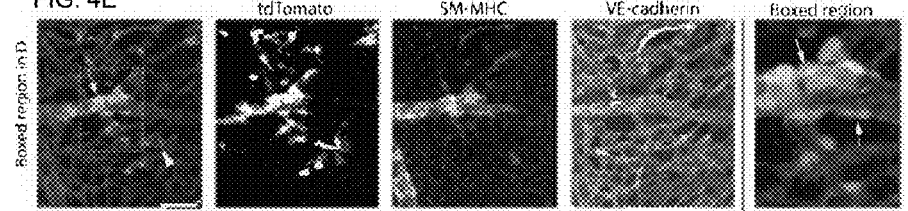
Figure 4F:
Figure 4G:
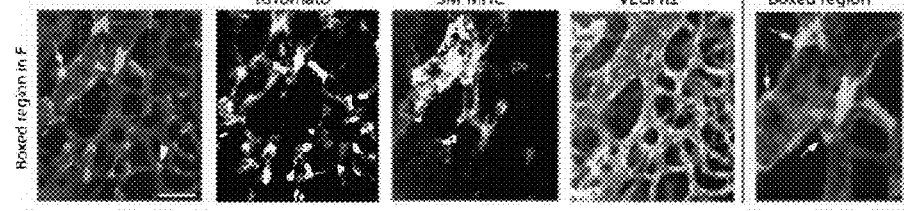

The above described composition and arrangement of epicardial-derived clones suggests that pericytes differentiate into caSMCs. However, direct lineage tracing of pericytes is required to confirm this sequence of events. NG2 and Notch3 are well established pericyte markers in other tissues. In the myocardium of the developing ventricle free walls, NG2- and Notch3-positive cells on the microvasculature always expressed PDGFRβ and wrapped vessels (FIG. 2FH), which identified them as cardiac pericytes (FIG. 2). NG2 and Notch3 also completely overlapped (n=185 cells counted, data not shown). To test if pericytes differentiate into smooth muscle, we performed lineage tracing using two independent mouse lines, NG2-CreER and Notch3-CreER. In embryos containing either the NG2-CreER or Notch3-CreER allele coupled with the fluorescent Cre reporter gene Rosa$^{tdtomato}$, pericytes, but not caSMCs, were labeled by injecting tamoxifen at either e10.5 or e11.5. This restricts Cre activity to a time point after pericytes had formed but before caSMCs appear (FIG. 4A). If caSMCs arise from pericytes, this strategy should result in lineage labeled caSMCs, i.e. tdtomato$^+$ (FIG. 4B). Importantly, no labeling was detected in the absence of tamoxifen (FIG. 4C and data not shown). In contrast, immunostaining injected hearts at e15.5 or e16.5 revealed that SM-MHC$^+$ caSMCs also expressed the tdtomato lineage label when recombination was induced with either NG2-CreER (FIG. 4D,E) or Notch3-CreER (FIG. 4F,G). A potential confounding factor is that both transgenes exhibited sporadic labeling in cardiomyocytes (Ozerdem et al., 2001), which was more rare in Notch3-CreER (FIG. 4D,F). However, control experiments showed that cardiomyocyte lineage tracing never labeled caSMCs (data not shown). Together, lineage tracing data from two independent Cre lines indicate that pericytes differentiate into caSMCs.

Pericytes in PDGFRβ Knockouts.

Figure 5A:
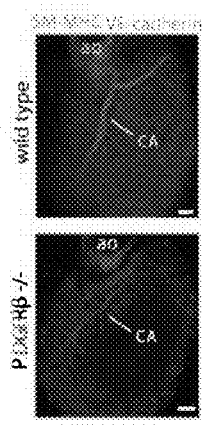
FIG. 5A-5D. Coronary artery smooth muscle is dramatically decreased in PDGFRβ-null mice.
Figure 5B:
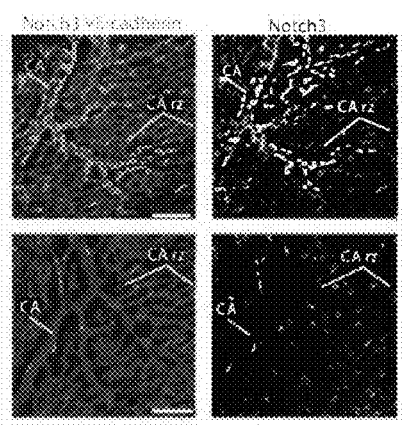
Figure 5C:
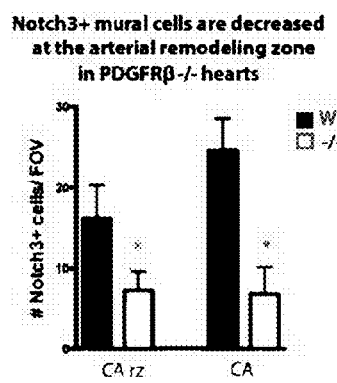
Figure 5D:
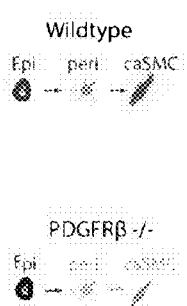

To gain further evidence that pericytes were caSMC progenitors, we analyzed mutants with deficient caSMC layers and asked if this phenotype was correlated with defects in pericytes at the arterial maturation zone. PDGFRβ-null mice have dramatically reduced caSMCs (FIG. 5A); however, they undergo vascular remodeling exhibiting a recognizable arterial remodeling zone and CA (FIG. 5B). Analyzing the total number of Notch3$^+$ pericytes at the remodeling zone revealed that they were significantly decreased (FIG. 5B,C). Pericytes and caSMCs were not completely gone (FIG. 5B,C) suggesting the presence of a very inefficient compensatory mechanism. The coincident decrease in pericytes and caSMC support a model where pericytes are progenitors that are required for smooth muscle formation, and that PDGFRβ functions at the surface to induce the first transition of the pathway from epicardial cell to pericyte (FIG. 5D).

Notch3 in the Pericyte to caSMC Transition.

To identify molecular regulators of the pericyte to caSMC differentiation step, we characterized the expression of mural cell markers at the arterial remodeling zone. Among those investigated, Notch3 was dramatically upregulated in the region where SM-MHC protein expression was initiated (FIG. 6A,B). In fact, the arterial remodeling zone can be identified based on Notch3 staining intensity without visualizing vessel structure (FIG. 6A). This pattern was in contrast to PDGFRβ, which was uniformly expressed in mural cells throughout the vasculature (FIG. 6A,B). Jagged-1 has been shown to be a major ligand for Notch3 in other organs, where it is expressed in arterial endothelium and stimulates smooth muscle differentiation including inducing the expression of SM-MHC. We found high levels of Jagged-1 to be specifically expressed at arterial remodeling zones where SM-MHC$^+$ cells were developing and in CAs (FIG. 6C and FIG. 14). Given that Jagged-1 has previously been identified as a shear stress-induced molecule in vitro, we investigated whether it could be regulated by blood flow in the heart. Coronary vessels are initially unperfused, but begin to receive blood flow after they attach to the aorta. This time point correlated with the onset of robust Jagged-1 expression in endothelial cells of vessels directly downstream of the attachment site (FIG. 6D-WT and FIG. 14). We analyzed a model of delayed CA stem attachment to the aorta, Isl1 heterozygosity (Cai et al., 2008a), which postpones the initiation of blood flow. Immunostaining Isl1 mutant hearts revealed that Jagged-1 was only upregulated in arterial remodeling zones of e13.5 hearts that had formed CA stems on the aorta to receive blood flow (FIG. 6D,E). Isl1 mutant hearts also failed to upregulate Notch3 in pericytes suggesting that this change also requires signals downstream of blood flow (n=9, data not shown). In summary, Notch3 is upregulated in pericytes at the arterial remodeling zone while its ligand Jagged-1 is induced in endothelial cells in the same region following the initiation of blood flow suggesting that this receptor-ligand pair could trigger caSMC differentiation in coronary pericytes.

We next analyzed Notch3-deficient hearts to investigate whether this signaling pathway could be involved in the pericyte to caSMC transition. Notch3-null mice had relatively normal CA remodeling and arterial caliber, but displayed significantly reduced levels of SM-MHC at the two time points examined, e15.5 and e17.5 (FIG. 6F,G and data not shown). In contrast, pericytes were still present in large numbers in the absence of Notch3, and PDGFRβ staining appeared similar to wild type counterparts around capillaries and arteries (FIG. 6H). Thus, the epicardial to pericyte differentiation and arterial coverage is not severely affected, but the pericyte to caSMC transition is disrupted (FIG. 6I). These data show that coronary vessels upregulate Jagged-1 after attaching to the aorta to receive arterial blood flow, and that Notch3 is required for pericyte to caSMCs differentiation, possibly in response to Jagged-1 expression at the arterial remodeling zone.

NG2+ and Notch3+ Cells are Smooth Muscle Progenitors in the Kidney.

Figure 7A:
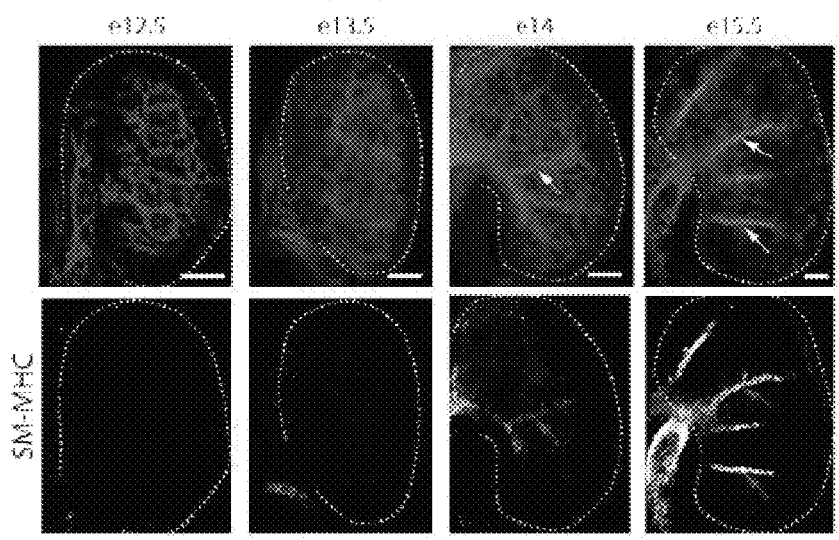
FIG. 7A-7C. NG2+ and Notch3+ cells differentiate into smooth muscle cells in the kidney.
Figure 7B:
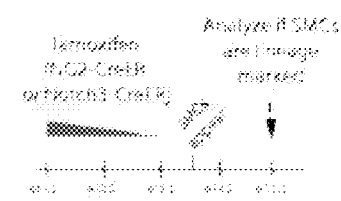
Figure 7C:
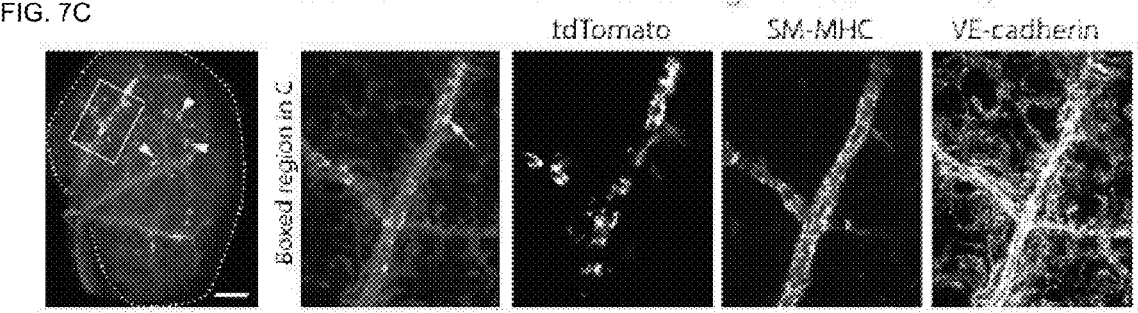

We next investigated whether the pericyte to smooth muscle transition occurs in the kidney, another organ who's internal arteries receive smooth muscle from the surface mesothelium. Characterization of smooth muscle development in the kidney using whole mount confocal microscopy showed that SM-MHC$^+$ cells first appear at e14 on developing intralobular arteries (FIG. 7A). As in the heart, NG2 also labels pericytes in the developing kidney (Lin et al., 2008). We therefore lineage traced either NG2- or Notch3-positive cells by inducing labeling of the Rosa$^{tdtomato}$ Cre reporter before smooth muscle appears (FIG. 7B). Both approaches resulted in robust lineage labeling of arterial smooth muscle cells in the kidney at e15.5 as well as other perivascular cells including those within the glomerulus (FIG. 7C). These data show that, similar to the heart, pericytes form an intermediate stage during this differentiation process in the kidney.

Here, we show, for the first time, that pericytes differentiate into smooth muscle cells during coronary artery development in the mouse heart and developing kidney. Previous identification of the epicardial-derived caSMC progenitor had been hampered by the fact that multiple developmental pathways occur downstream of epicardial differentiation. We have overcome this hurdle by using clonal analysis to label differentiation steps downstream of a single epicardial cell. This single cell tracing analyzes whether cells are clonally related eliminating one caveat of population level Cre labeling experiments where a mistake in the cell types expressing Cre can produce misleading results. Our clonal analysis of epicardial-derived cells identified vascular pericytes as being lineage related to caSMCs. The temporal presence and position of pericytes in epicardial-derived clones suggested that pericytes were the intermediate differentiation step between the epicardium and smooth muscle. This sequence of events was confirmed by direct pericyte lineage tracing using two independent pericyte Cre lines. In addition, pericytes were the most numerous epicardial-derived cell types at the CA remodeling zone where they wrapped developing arteries, a location that would allow them to respond to arterial maturation signals. Thus, we used complimentary lineage analysis experiments consisting of clonal and population-based tracing to show that pericytes, the most prominent epicardial-derived cell type around arterializing vessels, are progenitors for caSMCs.

Figures 8A, 8B:
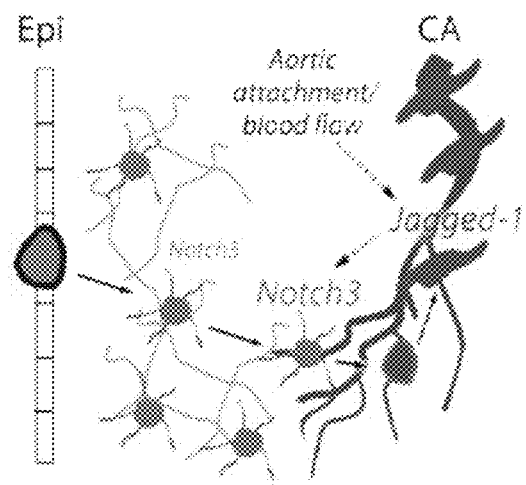
FIG. 8A-8B. Model and Summary.

Since pericytes wrap all small coronary vessels, we explored the signals that trigger their differentiation into caSMCs specifically at CA remodeling zones. We found that upon attachment to the aorta and establishment of blood flow, coronary endothelial cells downstream of the attachment site, which presumably receive the strongest blood flow, induce Jagged-1. Jagged-1 was not robustly expressed in a model of delayed aortic attachment and delayed initiation of blood flow. The Jagged-1 ligand Notch3 was upregulated in pericytes at the arterial remodeling zone, and caSMCs failed to differentiate in Notch3-null hearts. A delay in smooth muscle differentiation in the absence of Notch3 and Jagged-1 has been observed in other organ systems, however nothing is known about their roles in caSMC differentiation. Furthermore, due to the previous lack of knowledge of the lineage relationship between pericytes and smooth muscle cells, we are the first to show the importance of Notch3 signaling in stimulating the pericyte to smooth muscle transition. Jagged-1 and Notch signaling has been reported to be upregulated by sheer stress in vitro, but we provide the first evidence that this occurs in vivo following coronary plexus attachment to the aorta. Together, our data support a working model (FIG. 8) where epicardial cells differentiate into Notch3$^{low}$ pericytes that cover the entire coronary plexus as it populates the myocardium. Then, the pericytes located on plexus vessels that receive blood flow-induced Jagged-1 upregulate Notch3 and differentiate into caSMCs. Thus, blood flow specifies the site of arterial development in the coronary vascular plexus by stimulating vessel remodeling and pericyte differentiation into smooth muscle.

Our observations on the pericyte to smooth muscle transition are consistent with studies analyzing the timing of epicardial differentiation and its emergence into the myocardium. Studies dissecting the role of PDGFRs, TCF21, and Myocardin-Related Transcription Factors have provided evidence that the decision to differentiate into either the cardiac fibroblast or caSMC lineage occurs in epicardial cells at the heart's surface. In addition, progression down the caSMC lineage occurs early in development, mostly between e10.5 and 12.5. We show that endothelial cells migrating directly beneath the epicardium at this time point acquire pericytes and pericytes within caSMC containing clones are usually located near the heart's surface as well as deeper layers. Thus, migrating coronary vessels could trigger adjacent epicardial cells to differentiate into pericytes at the surface and support their movement into the myocardium along with invading endothelial cells. Then, the subset of these pericytes that traveled to arterializing vessels receives signals to become caSMCs. Clones also generally segregated between those containing pericytes/caSMCs and those with other cell types not positive for our cell type specific markers, likely fibroblasts, the latter of which did not integrate into the smooth muscle layer even when directly adjacent to the artery. Together, these findings provide strong evidence that two different epicardial derived pathways diverge at the surface of the heart where the pericyte/caSMC lineage travels along vessels as they invade the myocardium to provide the different mural cells of the coronary vasculature.

Analyzing pericyte-caSMC clones in adults showed that caSMC related pericytes persist after development is complete. Labeled cells in the adult heart were found in surprisingly tight clusters. This suggests that embryonic pericytes within caSMC clones were not merely an intermediate cell type that is depleted during development, but that cells not differentiating remain and function as cardiac pericytes throughout life. The tight clustering in adult hearts also indicate that pericytes travel very little along a vessel once they establish their location during development, at least in this organ. The embryonic heart has thus developed an efficient method of distributing smooth muscle progenitors, which maintain their cell-type specific function as pericytes at vessels that do not receive arterial blood flow and differentiation signals.

Studies in the adult heart and other adult tissues report that perivascular cells are a heterogeneous population with mesenchymal stem cell properties that can contribute to tissue fibrosis. Because the majority of caSMCs arise from the epicardium, we characterized epicardial-derived cells at the coronary artery remodeling zone. These were found to be almost exclusively either PDGFRβ$^+$Notch3$^+$NG2$^+$PDGFRα$^-$ (pericytes) or PDGFRβ$^-$Notch3$^-$ PDGFRα$^+$ (fibroblasts) suggesting less heterogeneity in the epicardial-derived cellular compartment at this age. This could be due to development being an early and protected stage in the animal's life or that the cellular milieu is more complex in the adult when immunity is active. Additional complexity is likely induced in tissue injury models. Although lineage tracing shows that pericytes are a large source, our data does not exclude other pathways to caSMC development. In fact, developmental studies have shown that an unidentified compensatory progenitor can provide caSMC if the epicardium is inhibited, although this source predisposes the arteries to disease. Regardless, the description of pericytes as progenitors and their presence in the adult identifies them as cells that can be utilized to produce new caSMCs during CA regeneration. Identifying the cellular pathway between the epicardium and smooth muscle is therefore important, particularly since it is known that epicardial cells do not enter the adult heart, even after myocardial infarction. Our data showing that pericytes are coronary artery smooth muscle progenitors and that they persist in the adult means that pericytes could be targeted without relying on the original progenitors (epicardial cells) being transported to form new collateral arteries.

Experimental Procedures

Animals. All animal experiments were performed according to protocols approved by the Stanford University Institutional Animal Care and Use Committee (IACUC). Mouse strains used: CD1 mice were used for wild type analysis and obtained from Charles River. NG2-CreER$^{B6.Cg-Tg(Cspg4-cre/Esr1*)BAkik/J}$ (Zhu et al., 2011), NG2-DsRed$^{(cspg4-DsRed.T1)1Akik/J}$, PDGFR-α$^{B6.129S4-Pdgfratm11(EGFP)Sor/J}$, α-MHC-Cre$^{Tg(Myh6-cre)1Jmk/J}$, MADM TG/TG$^{lis2tm2(ACTB-tdTomato,-EGFP)Luo/J}$, MADM GT/GT$^{lis2tm1(ACTB-EGFP,-tdTomato)Luo/J}$, Rosa-tdTomato$^{B6.Cg-Gt(ROSA)26Sortm9(CAG-tdTomato)Hze/J}$, PDGFRβ flox$^{129S4/SvJae-Pdgfrbtm11Sor/J}$ and Rosa-mTmG$^{Gt(ROSA)26Sortm4(ACTB-tdTomato,-EGFP)Luo/J}$ were all obtained from Jackson Laboratories. Conditional PDGFRβ flox animals were converted to full knockouts by crossing with HPRT-Cre females. Isl1 heterozygous (Cai et al., 2008a), Tbx18-Cre (Cai et al., 2008b), Notch3-CreER (Fre et al., 2011) and Notch3 (Krebs et al., 2003) have been previously described.

Immunohistochemistry and imaging. Staged embryonic hearts were obtained by timed pregnancies (morning plug designated e 0.5) and were dissected and fixed in 4% paraformaldehyde, washed and stored at 4° C. in phosphate buffered saline (PBS). Whole mount fluorescence microscopy was performed on intact hearts. Staining was performed in 1.5 ml tubes subjected to constant rotation. Primary antibodies were diluted in blocking solution (5% goat serum, 0.5% TritonX-100 in PBS) and incubated with tissues overnight at 4° C. Tissues were then washed with PBT (PBS with 0.5% TritonX-100) four times for one hour before another overnight incubation with secondary antibodies diluted in blocking solution. Specimens were then washed again, placed in Vectashield (Vector Labs #H-1000), and imaged using an inverted Zeiss LSM-700 confocal microscope. Images were digitally captured and processed using Zeiss Zen software (2011).

The following primary antibodies were used: VE-cadherin (BD Biosciences, 550548, 1:100), PDGFRβ (R&D Systems, #BAF1042 1:50; eBioscience 14-1402-81, 1:100), Notch3 (Santa Cruz Biotechnology #M-134 1:100), SM-MHC (Biomedical Technologies, BT-562, 1:300), VEGFR2 (R&D Systems AF644, 1:125); Jagged-1 (R&D Systems AF599, 1:125); Secondary reagents were Alexa Fluor conjugated antibodies (405, 488, 555, 637) from Life technologies used at 1:250 or streptavidin conjugates (Life technologies #S21374) used at 1:500.

Quantification (distance, fluorescence, and cell numbers) in whole mount preparations. In FIG. 1H, distance of SM-MHC$^{low}$ cells from the epicardium was measured from Z-plane views of whole mount confocal images using Zeiss Zen software. Fluorescence intensity values were calculated from single Z-planes using the same software package. For FIG. 1G, individual cells in single Z-planes were encircled and intensity values in the SM-MHC channel were recorded for mural cells surrounding the capillary plexus (n=16), remodeling zone (n=16), and mature arteries (n=16) from 4 different hearts each. For FIG. 5B, values in the PDGFRβ (n=9 cells/region from 3 hearts), Notch3 (n=21 cells/region from 7 hearts), and SM-MHC (n=15 cells/region from 3 hearts) channels were recorded. For FIG. 10B, localization of PDGFRα$^+$ and PDGFRβ$^+$ cells was measured using the profile option where fluorescent intensities are graphed along a line drawn across the XY-plane of a confocal image. Quantification of PDGFRβ, NG2, and Notch3 overlap (mentioned in the text and shown in FIG. 2F,G) was performed by randomly designating a field of view, encircling all the cells positive for either PDGFRβ or NG2, and counting the number of those circled also positive for the additional markers. Number of cells analyzed is stated in FIG. 2H counted from 3-4 hearts per marker, each from multiple litters.

Clonal analysis. Mice were bred so that embryos receive each of three alleles: Tbx18-Cre, a MADM GT cassette, and a TG cassette (Zong et al., 2005). Embryonic hearts were isolated at e13.5, e15.5 and 3-5 weeks of age and immunostained with antibodies for VE-cadherin, SM-MHC and PDGFRβ, and imaged as described above. For adults, 50 μm cryosectioning was performed and the sections were stained with the staining protocol as described above. Clusters of labeled cells were considered clonal if they were clearly distinct and at least 100 μm away from other labeled cells. For e13.5, e15.5 and adult clones a total of 12, 13 and 7 caSMC clones were quantified, respectively. Cell identities were assigned by the immunostaining criteria described in the main text and assessed by two individual researchers in the laboratory. Depth below the epicardium was analyzed using measurement tools included in the Zeiss Zen software (FIG. 13A). Quantification of pericytes, caSMCs and other cell types included all e15.5 clonal cells from 14 clones where no cells were excluded. In total, n values were 91 for epicardial cells, 249 for pericytes, 37 for caSMCs, 150 for other cell types.

Lineage tracing. Both NG2-CreER and Notch3-CreER males were crossed to Rosa-tdTomato reporter mice. Cre activity was activated by tamoxifen that was dissolved in corn oil and delivered to pregnant dames by intraperitoneal injection at either e10.5 or 11.5 (4 mg) with identical results. Dames impregnated by NG2-CreER and Notch3-CreER males were sacrificed at e15.5. Embryonic hearts and kidneys were stained with SM-MHC, PDGFRβ and VE-cadherin as described above before each cell type was assessed for lineage labeling. NG2-CreER traced smooth muscle was observed in 10 hearts/kidneys from three different litters. Notch3-CreER traced smooth muscle was observed in 11 hearts and kidneys from three two litters.

PDGFRβ mutant analysis. A total of 12 mutant hearts from 5 litters were analyzed all of which showed the same phenotype. For FIG. 5C, the number of Notch3$^+$ cells was recorded from a total of 7 wild type and 5 mutant hearts from 4 embryo litters from multiple 15,000 μm$^2$ fields of view: remodeling zone (Wt: n=19 fields; −/−: n=11 fields) and mature arteries (Wt: n=11 fields; −/−: n=11 fields).

Notch3 mutant analysis. Embryos were collected from Notch3 heterozygous crosses, and the hearts immunostained for VEGFR2, SM-MHC, and PDGFRβ as described above. A total of 20 mutants hearts from 10 litters from time points e15.5 and 17.5 were analyzed, all of which showed the same phenotype. For quantification in FIG. 6G, 9 mutant and 10 wild type hearts from 6 litters were analyzed (heterozygous hearts were not included in this analysis). Confocal z-stacks (with 14 μm intervals between z-planes) through the right lateral side of each heart were collected and imported into ImageJ (NIH). The "segmented line" tool was used to measure the total length of the right coronary artery (and its auxiliary branches) covered either partially or fully by SM-MHC$^+$ cells. Discontinuous lengths of smooth muscle coverage were summed for each heart.

Isl1 mutant heart analysis. Embryos were collected at e13.5 from crosses between Isl1 heterozygous and wild type mice. The hearts were immunostained for Jagged-1, SM-MHC, and VE-Cadherin as described above. A total of 27 heterozygous and 26 wild type hearts from 5 litters were analyzed. Confocal z-stacks (with 14 μm intervals between z-planes) through the right lateral side of the each heart were collected and analyzed. For each heart, the relative fluorescence intensity of Jagged-1 was recorded as a range from absent or very low to very high expression.

Statistics. Statistical analyses were performed using SigmaPlot version 12.0 (Systat Software Inc) or Prism (Graphpad), where appropriate normality and variation were calculated. Data are represented as mean±standard deviation (sd). Mann-Whitney Rank Sum tests were performed as appropriate for two-group comparisons, and oneway ANOVA was performed for multiple-group (more than 2 groups) comparisons and post hoc analysis was used with a Holm-Sidak post hoc test. A p<0.05 was considered statistically significant. Samples sizes were chosen so that statistically significant values would be obtained.

Example 2

Visualization of Collateral Coronary Artery Growth

To induce the production of collateral coronary arteries, we performed permanent ligations of the left anterior descending coronary artery. This stops blood flow to a portion of the left ventricular heart wall and induces myocardial ischemia (see Porrello et al. (2013) PNAS 110(1): 187-92). Four days post ligation, whole mount imaging of arterial endothelial cells (Cx40+) and arterial smooth muscle (SMA+) reveals that new arterial segments form between the ligated and intact artery so that the ischemic tissue can now receive blood flow (FIG. 15). These arterial segments are never seen in controls. Our embryonic work showed that coronary artery smooth muscle is produced when the pericytes that surround capillaries differentiate into smooth muscle; and that the space between the arterial tips is filled with capillaries surrounded by pericytes. Therefore, the collateral arterial segments develop using these resident pericytes, stimulating them to transform into smooth muscle, even in a post-natal model.

REFERENCES

Acharya et al. (2012) *Development* 12 2139-49
Armulik et al. (2011) *Dev Cell* 21, 193-215.
Braitsch et al. (2012) *Dev Biol* 2 345-57.
Briot et al. (2014) *Dev Cell* 31, 707-721.
Buckingham et al. (2011) *Dev Cell* 21, 394-409.
Cai et al. (2008) *Nature* 1-13, 877-89.
Cai (2008) *Nature* 454, 104-108.
Cappellari et al. (2013) *Circ Res* 113, 341-347.
Chen (2014) *J Clin Invest* 124, 4899-4914.
Chen et al. (2014) *Development* 141, 4500-4512.
Chen (2015) *Stem Cells* 33, 557-73.
Ding (2012) *Nature* 481, 457-62.
Doi et al. (2006) The Journal of Biological Chemistry 281, 28555-28564.
Dulauroy (2012) *Nature Medicine* 18, 1262-1270.
Fre et al. (2011) *PLoS ONE* 10 e25785
Hellström (1999) *Development* 126, 3047-3055.
High (2008) Proceedings of National Academy of Sciences 105, 1955-1959.
Hofmann (2012) *Development* 139, 4449-4460.
Hood (1992) *Anat. Rec.* 2 291-300.
Jin et al. (2008) *Circ Res* 102, 1483-1491.
Kattan (2004) *Dev. Dyn* 230, 34-43.
Natalie et al. (2011) *Genes Cancer* 2, 1106-1116.
Kramann et al. (2014) *Cell Stem Cell* 16 51-66.
Krebs et al. (2003) *Genesis* 37, 139-143.
Liu et al. (2010) *Circ Res* 107, 860-870.
Majesky et al. (2011) *Circ Res* 108, 365-377.
Manderfield et al. (2012) *Circulation* 17, 314-23.
McCormick et al. (2001) Proceedings of National Academy of Sciences 98, 8955-8960
Mellgren et al. 2008 *Circ Res* 12 1393-401.
Miano et al. (1994) *Circ Res* 75, 803-812.
Mikawa et al. (1996) *Dev Biol* 174, 221-232.
Ozerdem et al. *Dev Dyn*. 2001 2 218-27.
Perez-Pomares et al. (2002) *Int. J. Dev. Biol.* 46, 1005-1013.
Peeters et al. (1997) *Developmental dynamics* 3 338-48.
Red-Horse et al. (2010) *Nature* 464, 549-553.
Rinkevich et al. (2012) *Nature Cell Biology* 14, 1251-1260.
Rubanyi G M. 2013 *Molecular Therapy* 4 725-38
Seidelmann et al. (2013) *Cell. Mol. Life Sci.* 25, 1-23.
Smith et al. (2011) *Circulation Research* 108, 15-26.
Stallcup 2013. *Dev Cell* 24, 563-564.
Theodoris et al. (2015) *Cell* 160, 1072-86.
Tian X et al. (2013) *Cell Research* 23, 1075-1090.
Trembley et al. (2015) *Development* 142, 21-30.
Wei et al. (2015) *Cardiovasc Res* 2, 287-94.
Wilm (2005) *Development* 132, 5317-5328.
Wu et al. (2012) *Cell* 151, 1083-1096.
Yang, K and Proweller, A. 2011. *J Biol Chem* 286, 13741-53.
Zhou et al. (2008) *Nature* 454, 109-113.
Zhou et al. (2011) *J. Clin. Invest* 121, 1894-1904.
Zhu et al. (2011) *Development* 138, 745-753.
Zong et al. (2005) *Cell* 121, 479-492.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of providing smooth muscle cells to a tissue in need thereof, the method comprising:
   isolating cells that are $PDGFR\beta^+Notch3^+NG2^+$ $PDGFR\alpha^-$ from epicardium tissue to provide an isolated population of epicardial-derived pericytes;
   contacting the tissue with the isolated population, at a site where Jagged1 is expressed in endothelial cells of the region,
   wherein the epicardial-derived pericytes differentiate into smooth muscle cells expressing smooth muscle myosin heavy chain.

2. The method of claim 1, wherein the tissue is a blood vessel.

3. The method of claim 1, wherein the tissue is an artery.

4. The method of claim 1, wherein the tissue is a coronary artery.

5. The method of claim 1, wherein the contacting is performed in vivo.

6. The method of claim 5, wherein the contacting is performed on an individual suffering from coronary artery damage.

7. The method of claim 1, wherein the tissue is a kidney.

8. The method of claim 1 wherein the pericytes are derived from fetal tissue.

9. The method of claim 1 wherein the pericytes are derived from adult tissue.

10. The method of claim 1, wherein the epicardial-derived pericytes are selected for expression of NG2, Notch3 and PDGFRβ.

* * * * *